US011446127B2

(12) United States Patent
Adamo et al.

(10) Patent No.: US 11,446,127 B2
(45) Date of Patent: Sep. 20, 2022

(54) INSUFFLATION APPARATUS AND METHODS

(71) Applicant: MannKind Corporation, Valencia, CA (US)

(72) Inventors: Benoit Adamo, Mount Kisco, NY (US); Brendan F. Laurenzi, Middlebury, CT (US); Chad C. Smutney, Watertown, CT (US)

(73) Assignee: MannKind Corporation, Valencia, CA (US)

( * ) Notice: Subject to any disclaimer, the term of this patent is extended or adjusted under 35 U.S.C. 154(b) by 1073 days.

(21) Appl. No.: 14/910,235

(22) PCT Filed: Aug. 5, 2014

(86) PCT No.: PCT/US2014/049817
§ 371 (c)(1),
(2) Date: Feb. 4, 2016

(87) PCT Pub. No.: WO2015/021064
PCT Pub. Date: Feb. 12, 2015

(65) Prior Publication Data
US 2016/0175079 A1    Jun. 23, 2016

Related U.S. Application Data

(60) Provisional application No. 61/862,484, filed on Aug. 5, 2013.

(51) Int. Cl.
*A61D 7/04*    (2006.01)
*A61M 15/00*    (2006.01)
(Continued)

(52) U.S. Cl.
CPC ................. *A61D 7/04* (2013.01); *A01K 15/04* (2013.01); *A61D 3/00* (2013.01); *A61M 11/00* (2013.01);
(Continued)

(58) Field of Classification Search
CPC ...... A61D 7/04; A61D 3/00; A61D 2003/003; A61D 2003/006; A61M 16/0003;
(Continued)

(56) References Cited

U.S. PATENT DOCUMENTS 2,498,051 A * 2/1950 Shipley ..................... A61D 3/00
119/729
2,549,303 A    4/1951 Friden
(Continued)

FOREIGN PATENT DOCUMENTS

CA    2536047 A1    3/2005
CA    2551182 C    8/2010
(Continued)

OTHER PUBLICATIONS

Exubera package insert, p. 1, 2008.
(Continued)

*Primary Examiner* — Annette Dixon
(74) *Attorney, Agent, or Firm* — K&L Gates LLP; Brian J. Novak; Giorgios N. Kefallinos

(57) ABSTRACT

An insufflation apparatus and methods for using same are disclosed. The apparatus is equipped with an interactive system for administering reproducible intratracheal aerosols in a consistent automated manner. The insufflation system is useful, in particular for use with experimental animals, including mice and rats and also for treating small animals via the pulmonary route in veterinary medicinal practice.

10 Claims, 13 Drawing Sheets

(51) Int. Cl.
*A61D 3/00* (2006.01)
*A61M 16/14* (2006.01)
*A61M 11/00* (2006.01)
*A61M 16/00* (2006.01)
*A01K 15/04* (2006.01)

(52) U.S. Cl.
CPC ........ *A61M 15/00* (2013.01); *A61M 16/0003* (2014.02); *A61M 16/0057* (2013.01); *A61M 16/14* (2013.01); *A61M 2016/0018* (2013.01); *A61M 2016/0024* (2013.01); *A61M 2202/064* (2013.01); *A61M 2205/07* (2013.01); *A61M 2205/3375* (2013.01); *A61M 2205/50* (2013.01); *A61M 2230/005* (2013.01); *A61M 2230/40* (2013.01); *A61M 2230/42* (2013.01); *A61M 2230/63* (2013.01); *A61M 2250/00* (2013.01)

(58) Field of Classification Search
CPC .. A61M 11/00; A61M 15/00; A61M 16/0057; A61M 16/14; A61M 2016/0018; A61M 2016/0024; A61M 2202/064; A61M 2205/07; A61M 2205/3375; A61M 2205/50; A61M 2230/005; A61M 2230/40; A61M 2230/42; A61M 2230/63; A61M 2250/00; A61M 11/02; A61M 16/00; A61M 16/0093; A61M 16/01; A61M 16/0463; A61M 16/0465; A61M 16/06; A61M 16/0672; A61M 16/107; A61M 16/18; A61M 2016/0027; A61M 2205/3317; A61M 2205/3592; A61M 2205/502; A61M 2205/505; A61M 2205/581; A61M 2205/584; A61M 2205/6081; A61M 2205/80; A61M 2230/201; A61M 2230/43; A61M 39/08; A61M 5/14; A61M 5/1407; A61M 5/1723; A01K 15/04; A22B 3/00; A61B 1/00087; A61B 1/2676; A61B 18/203; A61B 18/22; A61B 2017/00809; A61B 2018/00577; A61B 2018/00589; A61B 2018/00595; A61B 2018/00601; A61B 2018/00625; A61B 2018/225; A61B 2034/105; A61B 2034/107; A61B 2034/2051; A61B 2034/252; A61B 2090/373; A61B 2090/374; A61B 2090/3762; A61B 2090/378; A61B 2090/3941; A61B 2090/401; A61B 2090/506; A61B 2503/06; A61B 2503/40; A61B 34/10; A61B 34/20; A61B 42/10; A61B 5/0004; A61B 5/0022; A61B 5/055; A61B 5/062; A61B 5/1115; A61B 5/1116; A61B 5/1451; A61B 5/14532; A61B 5/4839; A61B 5/704; A61B 5/746; A61B 6/032; A61B 6/035; A61B 6/04; A61B 6/0428; A61B 6/0487; A61B 6/06; A61B 6/4283; A61B 6/4441; A61B 6/4464; A61B 6/467; A61B 6/508; A61B 6/542; A61B 6/547; A61B 6/589; A61B 90/361; A61B 90/37; A61B 90/40; A61B 90/50; A61B 90/57; A61G 10/005; A61G 10/02; A61G 10/04; A61G 11/009; A61G 13/02; A61G 13/04; A61G 13/06; A61G 13/108; A61G 2200/32; A61G 2203/30; A61G 2203/70; A61G 2203/72; A61G 2210/50; A61G 7/005; A61G 7/012; A61G 7/018; A61L 2/10; A61N 2005/1054; A61N 5/06; A61N 5/10; A61N 5/1001; A61N 5/103; A61N 5/1071; G01G 19/445; G06F 21/6245; G06Q 10/06; G06Q 10/0633; G06T 7/292; G06V 20/52; G06V 40/23; G16H 20/17; G16H 20/60; G16H 30/20; G16H 30/40; G16H 40/20; G16H 40/63; G16H 50/20; G16H 50/70; Y02A 90/10; Y10S 128/06; Y10S 128/12; Y10S 128/26

See application file for complete search history.

(56) References Cited

U.S. PATENT DOCUMENTS

| | | |
|---|---|---|
| 2,754,276 A | 7/1956 | Joseph et al. |
| D189,076 S | 10/1960 | Altman |
| 3,254,645 A * | 6/1966 | Rand .................. A61H 31/005 601/41 |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,673,698 A | 7/1972 | Guerard |
| 3,669,113 A | 8/1972 | Altounyan et al. |
| 3,687,137 A * | 8/1972 | Johnson .............. A61M 16/104 128/204.13 |
| 3,823,816 A | 7/1974 | Controullis et al. |
| 3,823,843 A | 7/1974 | Stephens et al. |
| 3,856,142 A | 12/1974 | Vessalo |
| 3,873,651 A | 3/1975 | Mosley, Jr. et al. |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |
| 4,212,297 A * | 7/1980 | Frosch .............. A61M 16/0465 128/204.18 |
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavener |
| 4,294,829 A | 10/1981 | Suzuki |
| 4,300,546 A | 11/1981 | Kruber |
| 4,356,167 A | 10/1982 | Kelly |
| D269,463 S | 6/1983 | Young et al. |
| 4,407,525 A | 10/1983 | Hoppe |
| 4,456,007 A | 6/1984 | Nakao et al. |
| 4,483,922 A | 11/1984 | Carpenter |
| D276,654 S | 12/1984 | Snellman-Wasenius et al. |
| 4,487,327 A | 12/1984 | Grayson |
| 4,520,808 A * | 6/1985 | LaBauve .............. A01K 13/001 128/200.14 |
| 4,524,769 A | 6/1985 | Wetterlin |
| 4,526,804 A | 7/1985 | Escallon |

(56) References Cited

U.S. PATENT DOCUMENTS

| | | |
|---|---|---|
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai et al. |
| 4,668,218 A | 5/1987 | Virtanen |
| 4,681,752 A | 7/1987 | Melillo |
| D295,321 S | 4/1988 | Hallworth |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,847,091 A | 7/1989 | Illum |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,981,625 A | 1/1991 | Rhim et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoefling |
| 5,017,383 A | 5/1991 | Ozawa et al. |
| 5,019,400 A | 5/1991 | Gombotz et al. |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,007 A | 5/1992 | Law et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,139,878 A | 8/1992 | Kim |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,196,049 A | 3/1993 | Coombs et al. |
| 5,201,308 A | 4/1993 | Newhouse |
| 5,203,768 A | 4/1993 | Haak et al. |
| 5,204,108 A | 4/1993 | Ilium |
| 5,208,998 A | 5/1993 | Dyler, Jr. |
| 5,215,739 A | 6/1993 | Kamishita et al. |
| D337,636 S | 7/1993 | Kocinski |
| D338,062 S | 8/1993 | Fair |
| D338,268 S | 8/1993 | Kobayashi et al. |
| 5,239,992 A | 8/1993 | Bougamont et al. |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Fair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A | 7/1994 | Andersson et al. |
| 5,333,106 A | 7/1994 | Lanpher et al. |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs et al. |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton |
| 5,469,750 A | 11/1995 | Lloyd et al. |
| 5,469,971 A | 11/1995 | Chilton et al. |
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstorm et al. |
| D370,255 S | 5/1996 | Yamamoto et al. |
| 5,513,630 A * | 5/1996 | Century ............ A61M 15/0028 128/203.12 |
| 5,514,646 A | 5/1996 | Chance et al. |
| 5,518,998 A | 5/1996 | Backstorm et al. |

(56) References Cited

U.S. PATENT DOCUMENTS

| | | |
|---|---|---|
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Fang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |
| 5,972,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed et al. |
| 5,981,488 A | 11/1999 | Hoffman |
| 5,983,893 A | 11/1999 | Wetterlin |
| 5,985,248 A | 11/1999 | Gordon et al. |

(56) References Cited

U.S. PATENT DOCUMENTS

| | | |
|---|---|---|
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystorm et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A | 6/2000 | Lindahl et al. |
| 6,077,543 A | 6/2000 | Gordon et al. |
| 6,080,762 A | 6/2000 | Allen et al. |
| 6,085,745 A | 6/2000 | Levander et al. |
| D428,486 S | 7/2000 | Schuckmann |
| 6,087,334 A | 7/2000 | Beeley et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,098,619 A | 8/2000 | Britto et al. |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,099,517 A | 9/2000 | Daughtery |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A | 11/2000 | Abrams |
| 6,153,613 A | 11/2000 | Ono et al. |
| 6,155,423 A | 12/2000 | Katzne et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | Shuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstorm et al. |
| 6,357,442 B1 | 3/2002 | Casper et al. |
| 6,358,058 B1 | 3/2002 | Strupat et al. |
| 6,358,924 B1 | 3/2002 | Hoffman |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Hermeling et al. |
| 6,386,195 B1 | 5/2002 | Coffee |
| 6,388,053 B1 | 5/2002 | Galloway et al. |
| 6,394,085 B1 | 5/2002 | Hardy et al. |
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |
| D460,173 S | 7/2002 | Harrison et al. |
| 6,415,784 B1 | 7/2002 | Christup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelberth et al. |
| 6,443,143 B1 | 9/2002 | Ishida et al. |
| 6,444,226 B1 | 9/2002 | Steiner et al. |
| 6,446,626 B1 | 9/2002 | Virtanen |
| 6,446,627 B1 | 9/2002 | Bowman et al. |
| 6,447,750 B1 | 9/2002 | Cutie et al. |
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |
| 6,468,507 B1 | 10/2002 | Cutie et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| 6,523,536 B2 | 2/2003 | Fugelsang et al. |

(56) References Cited

U.S. PATENT DOCUMENTS

| | | |
|---|---|---|
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,127 B2 | 4/2003 | Steiner |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson et al. |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelberth et al. |
| 6,630,169 B1 | 10/2003 | Bot et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B2 | 12/2003 | Myrman et al. |
| 6,672,304 B1 | 1/2004 | Casper et al. |
| 6,676,931 B2 | 1/2004 | Dugger, III |
| 6,679,255 B2 | 1/2004 | Pera |
| 6,681,767 B1 | 1/2004 | Patton et al. |
| 6,681,768 B1 | 1/2004 | Haaije de Boer et al. |
| 6,685,967 B1 | 2/2004 | Patton et al. |
| 6,698,421 B2 | 3/2004 | Attolini |
| 6,698,422 B2 | 3/2004 | Fugelsang et al. |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,729,328 B2 | 5/2004 | Raul |
| 6,737,045 B2 | 5/2004 | Patton |
| 6,745,761 B2 | 6/2004 | Christup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 | 6/2004 | Bonney et al. |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,797,258 B2 | 9/2004 | Platz et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,838,075 B2 | 1/2005 | Stevenson et al. |
| 6,838,076 B2 | 1/2005 | Platton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,881,423 B2 | 4/2005 | Dohi et al. |
| 6,884,435 B1 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |
| D506,680 S | 6/2005 | Saelzer |
| 6,904,907 B2 | 6/2005 | Speldrich et al. |
| 6,906,030 B2 | 6/2005 | Milstein |
| 6,916,354 B2 | 7/2005 | Elliot |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole et al. |
| D509,296 S | 9/2005 | Minshull et al. |
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Joregenson et al. |
| D511,208 S | 11/2005 | Pardonge et al. |
| D511,977 S | 11/2005 | Saelzer |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |

(56) References Cited

U.S. PATENT DOCUMENTS

| | | |
|---|---|---|
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,107,988 B2 | 9/2006 | Pinon et al. |
| D529,604 S | 10/2006 | Voung et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| D540,671 S | 4/2007 | Born |
| D541,151 S | 4/2007 | Born |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Hammer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,265,087 B1 | 9/2007 | Goke et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Mryman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| D566,549 S | 4/2008 | Russell |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Fang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |
| 7,794,754 B2 | 9/2010 | Feldstein et al. |
| 7,799,344 B2 | 9/2010 | Oberg |
| 7,803,404 B2 | 9/2010 | Hokenson |
| 7,820,676 B2 | 10/2010 | Leone-Bay et al. |
| D626,836 S | 11/2010 | Lien |
| D628,090 S | 11/2010 | Stuiber et al. |
| 7,833,549 B2 | 11/2010 | Steiner et al. |
| 7,833,550 B2 | 11/2010 | Steiner et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |
| D635,242 S | 3/2011 | Adamo |
| D635,243 S | 3/2011 | Kinsey |
| 7,913,688 B2 | 3/2011 | Cross |
| D636,867 S | 4/2011 | Polidoro et al. |
| D636,868 S | 4/2011 | Kinsey et al. |
| D636,869 S | 4/2011 | Laurenzi et al. |
| 7,919,119 B2 | 4/2011 | Straub et al. |
| 7,943,178 B2 | 5/2011 | Steiner et al. |
| 7,943,572 B2 | 5/2011 | Cheatham et al. |
| 7,954,491 B2 | 6/2011 | Hrkach |
| 7,959,609 B2 | 6/2011 | Gaydos et al. |
| D641,076 S | 7/2011 | Grunstad et al. |

(56) References Cited

U.S. PATENT DOCUMENTS

| | | | |
|---|---|---|---|
| D643,308 S | 8/2011 | Bergey | |
| D645,954 S | 9/2011 | Hately | |
| D647,195 S | 10/2011 | Clarke et al. | |
| D647,196 S | 10/2011 | Clarke et al. | |
| 8,037,880 B2 | 10/2011 | Zhu et al. | |
| 8,037,881 B2 | 10/2011 | Pentafragas | |
| 8,039,431 B2 | 10/2011 | Wilson et al. | |
| 8,047,203 B2 | 11/2011 | Young et al. | |
| D652,322 S | 1/2012 | Stuiber et al. | |
| 8,109,267 B2 | 2/2012 | Villax et al. | |
| 8,119,593 B2 | 2/2012 | Richardson | |
| D655,622 S | 3/2012 | Sadler et al. | |
| 8,133,514 B2 | 3/2012 | Milstein | |
| 8,146,588 B2 | 4/2012 | Steiner et al. | |
| 8,156,936 B2 | 4/2012 | Steiner et al. | |
| D659,020 S | 5/2012 | Kemner | |
| D659,022 S | 5/2012 | Kemner | |
| D660,956 S | 5/2012 | Zuyderhoudt | |
| 8,166,970 B2 | 5/2012 | Poole et al. | |
| 8,172,817 B2 | 5/2012 | Michaels et al. | |
| 8,196,576 B2 | 6/2012 | Kriksunov et al. | |
| 8,201,555 B2 | 6/2012 | Chawla | |
| 8,202,992 B2 | 6/2012 | Stevenson | |
| D663,830 S | 7/2012 | Sears | |
| D664,640 S | 7/2012 | Smutney et al. | |
| 8,215,300 B2 | 7/2012 | Steiner et al. | |
| 8,217,007 B1 | 7/2012 | Schteingart et al. | |
| 8,227,409 B2 | 7/2012 | Kraft | |
| 8,236,766 B2 | 8/2012 | Schteingart et al. | |
| 8,252,916 B2 | 8/2012 | Simard et al. | |
| 8,258,095 B2 | 9/2012 | Boss et al. | |
| 8,278,308 B2 | 10/2012 | Leone-Bay et al. | |
| 8,293,869 B2 | 10/2012 | Bossard | |
| 8,314,106 B2 | 11/2012 | Kraft | |
| D671,842 S | 12/2012 | Bergey | |
| D674,893 S | 1/2013 | Kinsey et al. | |
| 8,372,804 B2 | 2/2013 | Richardson | |
| 8,377,869 B2 | 2/2013 | Richardson | |
| 8,389,470 B2 | 3/2013 | Steiner | |
| 8,394,414 B2 | 3/2013 | Steiner et al. | |
| 8,408,200 B2 | 4/2013 | Clark et al. | |
| 8,420,604 B2 | 4/2013 | Hokenson | |
| 8,424,518 B2 | 4/2013 | Smutney | |
| 8,485,180 B2 | 7/2013 | Smutney et al. | |
| 8,486,894 B2 | 7/2013 | Schteingart et al. | |
| 8,499,757 B2 | 8/2013 | Smutney | |
| 8,512,932 B2 | 8/2013 | Wilson et al. | |
| 8,522,775 B2 | 9/2013 | Malhotra et al. | |
| 8,536,131 B2 | 9/2013 | Schteingart et al. | |
| 8,538,707 B2 | 9/2013 | Adamo et al. | |
| 8,539,946 B2 | 9/2013 | Esteve et al. | |
| 8,551,528 B2 | 10/2013 | Grant et al. | |
| 8,563,101 B2 | 10/2013 | Spallek | |
| 8,636,001 B2 | 1/2014 | Smutney | |
| 8,642,548 B2 | 2/2014 | Richardson et al. | |
| 8,671,937 B2 | 3/2014 | Steiner et al. | |
| 8,677,992 B2 | 3/2014 | Villax | |
| 8,763,606 B2 | 7/2014 | Mosier et al. | |
| 8,778,403 B2 | 7/2014 | Grant et al. | |
| 8,783,249 B2 | 7/2014 | Poole et al. | |
| D711,740 S | 8/2014 | Lien | |
| 8,808,786 B2 | 8/2014 | Jinks et al. | |
| 8,820,324 B2 | 9/2014 | Smith et al. | |
| 8,909,487 B2 | 12/2014 | Adamo et al. | |
| 8,925,726 B2 | 1/2015 | Bergey | |
| 9,041,925 B2 | 5/2015 | Adamo et al. | |
| 9,138,407 B2 | 9/2015 | Caponetti et al. | |
| 10,064,713 B2 * | 9/2018 | Im | A61D 7/04 |
| 2001/0020147 A1 | 9/2001 | Staniforth et al. | |
| 2001/0039442 A1 | 11/2001 | Gorge et al. | |
| 2002/0000225 A1 | 1/2002 | Schuler et al. | |
| 2002/0033177 A1 | 3/2002 | Ohki et al. | |
| 2002/0052381 A1 | 5/2002 | Bar-Or et al. | |
| 2002/0053344 A1 | 5/2002 | Davies et al. | |
| 2002/0053347 A1 | 5/2002 | Ziaee | |
| 2002/0065239 A1 | 5/2002 | Caplan et al. | |
| 2002/0088462 A1 | 7/2002 | Genova et al. | |
| 2002/0101590 A1 | 8/2002 | Shimaoka | |
| 2002/0144680 A1 | 10/2002 | Nilsson et al. | |
| 2002/0161001 A1 | 10/2002 | Kanstrup et al. | |
| 2003/0000524 A1 | 1/2003 | Andersson et al. | |
| 2003/0010794 A1 | 1/2003 | Herdtle et al. | |
| 2003/0013641 A1 | 1/2003 | Steiner et al. | |
| 2003/0017211 A1 | 1/2003 | Steiner | |
| 2003/0018276 A1 * | 1/2003 | Mansy | A61B 7/003 600/529 |
| 2003/0053960 A1 | 3/2003 | Heijerman et al. | |
| 2003/0064097 A1 | 4/2003 | Patel et al. | |
| 2003/0068378 A1 | 4/2003 | Chen et al. | |
| 2003/0099636 A1 | 5/2003 | Epshtein et al. | |
| 2003/0136405 A1 | 7/2003 | Goede et al. | |
| 2003/0194420 A1 | 10/2003 | Holl et al. | |
| 2003/0235538 A1 | 12/2003 | Zirenberg | |
| 2004/0024180 A1 | 2/2004 | Drauz | |
| 2004/0025875 A1 | 2/2004 | Reber et al. | |
| 2004/0034014 A1 | 2/2004 | Kanstrup et al. | |
| 2004/0038865 A1 | 2/2004 | Gelber et al. | |
| 2004/0053819 A1 | 3/2004 | Dodd et al. | |
| 2004/0062722 A1 | 4/2004 | Gonda et al. | |
| 2004/0076588 A1 | 4/2004 | Batycky et al. | |
| 2004/0077528 A1 | 4/2004 | Steiner et al. | |
| 2004/0096403 A1 | 5/2004 | Steiner | |
| 2004/0107963 A1 | 6/2004 | Finlay et al. | |
| 2004/0121964 A1 | 6/2004 | Madar et al. | |
| 2004/0138099 A1 | 7/2004 | Draeger | |
| 2004/0151059 A1 | 8/2004 | Robert, II et al. | |
| 2004/0151774 A1 | 8/2004 | Pauletti et al. | |
| 2004/0157928 A1 | 8/2004 | Kim et al. | |
| 2004/0163648 A1 * | 8/2004 | Burton | A61M 16/0683 128/204.21 |
| 2004/0182387 A1 | 9/2004 | Steiner et al. | |
| 2004/0187869 A1 | 9/2004 | Bjorndal et al. | |
| 2004/0204439 A1 | 10/2004 | Staniforth et al. | |
| 2004/0204440 A1 | 10/2004 | Staniforth et al. | |
| 2004/0211419 A1 | 10/2004 | Eason et al. | |
| 2004/0211420 A1 | 10/2004 | Minshull | |
| 2004/0234615 A1 | 11/2004 | Sabetsky | |
| 2004/0234616 A1 | 11/2004 | Sabetsky | |
| 2004/0241232 A1 | 12/2004 | Brown et al. | |
| 2004/0247628 A1 | 12/2004 | Lintz et al. | |
| 2004/0250812 A1 | 12/2004 | Davies et al. | |
| 2005/0000518 A1 | 1/2005 | Dunkley et al. | |
| 2005/0039743 A1 | 2/2005 | Taylor | |
| 2005/0043228 A1 | 2/2005 | DeFelippis et al. | |
| 2005/0043247 A1 | 2/2005 | Trunk et al. | |
| 2005/0056281 A1 | 3/2005 | Snow | |
| 2005/0070469 A1 | 3/2005 | Bloom | |
| 2005/0080000 A1 | 4/2005 | Thurow et al. | |
| 2005/0119604 A1 | 6/2005 | Bonney et al. | |
| 2005/0124644 A1 | 6/2005 | Nilsson et al. | |
| 2005/0147581 A1 | 7/2005 | Zamiri et al. | |
| 2005/0153874 A1 | 7/2005 | Cheatham et al. | |
| 2005/0155601 A1 | 7/2005 | Steiner et al. | |
| 2005/0183723 A1 | 8/2005 | Pinon et al. | |
| 2005/0187749 A1 | 8/2005 | Singley | |
| 2005/0214251 A1 | 9/2005 | Pohl et al. | |
| 2005/0252508 A1 | 11/2005 | Koerner | |
| 2005/0265927 A1 | 12/2005 | Lee | |
| 2005/0274378 A1 | 12/2005 | Bonney et al. | |
| 2006/0000469 A1 | 1/2006 | Tseng | |
| 2006/0003316 A1 | 1/2006 | Simard et al. | |
| 2006/0040953 A1 | 2/2006 | Leone-Bay et al. | |
| 2006/0041133 A1 | 2/2006 | Stevenson et al. | |
| 2006/0062740 A1 | 3/2006 | Rand | |
| 2006/0099269 A1 | 5/2006 | Cheatham et al. | |
| 2006/0120969 A1 | 6/2006 | Nilsson et al. | |
| 2006/0153778 A1 | 7/2006 | Gelber et al. | |
| 2006/0160722 A1 | 7/2006 | Green et al. | |
| 2006/0165756 A1 | 7/2006 | Catani et al. | |
| 2006/0239933 A1 | 10/2006 | Nilsson et al. | |
| 2006/0239934 A1 | 10/2006 | Cheatham et al. | |
| 2006/0243275 A1 | 11/2006 | Ruckdeschel et al. | |
| 2006/0249419 A1 | 11/2006 | Taylor et al. | |
| 2006/0260777 A1 | 11/2006 | Rashba-Step et al. | |

(56) References Cited

U.S. PATENT DOCUMENTS

| | | |
|---|---|---|
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Oberg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0175314 A1 | 8/2007 | Wanne |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127974 A1 | 6/2008 | Lastow |
| 2008/0129791 A1 | 6/2008 | King et al. |
| 2008/0135047 A1* | 6/2008 | Johnson ............ A61M 15/0028 128/203.15 |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Messi |
| 2008/0295833 A1 | 12/2008 | Rohrschneider et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0126731 A1* | 5/2009 | Dunsmore ........ A61M 16/0003 128/203.12 |
| 2009/0134051 A1 | 5/2009 | Rapp et al. |
| 2009/0149727 A1 | 6/2009 | Truitt et al. |
| 2009/0151720 A1* | 6/2009 | Inoue ...................... A22B 3/00 128/203.12 |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0211003 A1* | 8/2010 | Sundar ............... A61M 5/16813 604/67 |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1* | 1/2011 | Gumaste ................. A61M 11/02 128/200.23 |
| 2011/0003004 A1 | 1/2011 | Hokenson |
| 2011/0011394 A1 | 1/2011 | Edwards et al. |
| 2011/0083667 A1 | 4/2011 | Briant |
| 2011/0158935 A1 | 6/2011 | Kraft |
| 2011/0183901 A1 | 7/2011 | Cheatham |
| 2011/0223116 A1* | 9/2011 | Century ............... A61M 15/009 424/45 |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0291781 A1* | 11/2012 | Kaufmann ........ A61M 15/0003 128/203.15 |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |
| 2014/0100158 A1 | 4/2014 | Richardson et al. |
| 2014/0187490 A1 | 7/2014 | Richardson et al. |
| 2014/0199398 A1 | 7/2014 | Grant et al. |
| 2014/0227359 A1 | 8/2014 | Leone-Bay et al. |
| 2014/0243530 A1 | 8/2014 | Stevenson et al. |
| 2014/0271888 A1 | 9/2014 | Grant et al. |
| 2014/0290654 A1 | 10/2014 | Poole et al. |
| 2014/0302151 A1 | 10/2014 | Leone-Bay et al. |
| 2014/0308358 A1 | 10/2014 | Oberg et al. |
| 2014/0315953 A1 | 10/2014 | Leone-Bay et al. |
| 2015/0031609 A1 | 1/2015 | Steiner et al. |
| 2015/0045295 A1 | 2/2015 | Smutney et al. |
| 2015/0052977 A1 | 2/2015 | Adamo et al. |
| 2015/0065422 A1 | 3/2015 | Kraft |
| 2015/0080298 A1 | 3/2015 | Costello et al. |
| 2015/0108023 A1 | 4/2015 | Bergey |
| 2015/0122258 A1 | 5/2015 | Steiner et al. |
| 2015/0150980 A1 | 6/2015 | Leone-Bay et al. |
| 2015/0174210 A1 | 6/2015 | Boss et al. |
| 2015/0196724 A1 | 7/2015 | Adamo et al. |
| 2015/0226656 A1 | 8/2015 | Adamo et al. |
| 2015/0231067 A1 | 8/2015 | Mann |
| 2015/0246188 A1 | 9/2015 | Steiner et al. |
| 2015/0283069 A1 | 10/2015 | Smutney et al. |

(56) References Cited

U.S. PATENT DOCUMENTS

| | | |
|---|---|---|
| 2015/0283213 A1 | 10/2015 | Costello et al. |
| 2015/0290132 A1 | 10/2015 | Gelber et al. |
| 2015/0359744 A1 | 12/2015 | Hokenson et al. |

FOREIGN PATENT DOCUMENTS

| | | |
|---|---|---|
| CN | 101851213 | 10/2010 |
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 640354 B1 | 12/2001 |
| EP | 1364967 | 11/2003 |
| EP | 325885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 1990/013285 | 11/1990 |
| WO | 1991/004011 | 4/1991 |
| WO | 1991/006287 | 5/1991 |
| WO | 1991/016038 | 10/1991 |
| WO | 1991/016882 | 11/1991 |
| WO | 1991/019524 | 12/1991 |
| WO | 1992/004069 | 3/1992 |
| WO | 1992/008509 | 5/1992 |
| WO | 1993/002712 | 2/1993 |
| WO | 1993/014110 | 7/1993 |
| WO | 1993/017728 | 9/1993 |
| WO | 1993/018754 A1 | 9/1993 |
| WO | 1994/000291 | 1/1994 |
| WO | 1994/008552 | 4/1994 |
| WO | 1994/008599 | 4/1994 |
| WO | 1994/019041 | 9/1994 |
| WO | 1994/023702 | 10/1994 |
| WO | 1994/025005 A1 | 11/1994 |
| WO | 1995/000127 A1 | 1/1995 |
| WO | 1995/005208 | 2/1995 |
| WO | 1995/011666 | 5/1995 |
| WO | 1995/024183 A1 | 9/1995 |
| WO | 1995/031979 | 11/1995 |
| WO | 1995/034294 | 12/1995 |
| WO | 1996/001105 | 1/1996 |
| WO | 1996/005810 | 2/1996 |
| WO | 1996/013250 | 5/1996 |
| WO | 1996/022802 A | 8/1996 |
| WO | 1996/027386 A1 | 9/1996 |
| WO | 1996/032149 | 10/1996 |
| WO | 1996/036314 | 11/1996 |
| WO | 1996/036317 A1 | 11/1996 |
| WO | 1996/040206 A1 | 12/1996 |
| WO | 1997/001365 | 1/1997 |
| WO | 1997/004747 | 2/1997 |
| WO | 1997/025086 A2 | 7/1997 |
| WO | 1997/030743 | 8/1997 |
| WO | 1997/035562 A1 | 10/1997 |
| WO | 1997/046206 | 12/1997 |
| WO | 1997/049386 | 12/1997 |
| WO | 1998/026827 A1 | 6/1998 |
| WO | 1998/039043 | 9/1998 |
| WO | 1998/041255 A2 | 9/1998 |
| WO | 1998/043615 | 10/1998 |
| WO | 1999/014239 A1 | 3/1999 |
| WO | 1999/018939 A1 | 4/1999 |
| WO | 1999/032510 A1 | 7/1999 |
| WO | 1999/033862 | 7/1999 |
| WO | 1999/052506 | 10/1999 |
| WO | 2000/12116 | 3/2000 |
| WO | 2000/033811 A2 | 6/2000 |
| WO | 2000/059476 A1 | 10/2000 |
| WO | 2000/071154 A2 | 11/2000 |
| WO | 2001/000654 | 1/2001 |
| WO | 2001/081321 A | 1/2001 |
| WO | 2001/049274 A2 | 7/2001 |
| WO | 2001/051071 | 7/2001 |
| WO | 2001/052813 A1 | 7/2001 |
| WO | 2001/066064 | 9/2001 |
| WO | 2001/068169 | 9/2001 |
| WO | 2001/097886 A1 | 12/2001 |
| WO | 2001/007107 | 2/2002 |
| WO | 2002/011676 | 2/2002 |
| WO | 2002/012201 A1 | 2/2002 |
| WO | 2002/047659 A2 | 6/2002 |
| WO | 2002/058735 | 8/2002 |
| WO | 2002/059574 A1 | 8/2002 |
| WO | 2002/067995 A1 | 9/2002 |
| WO | 2002/085281 | 10/2002 |
| WO | 2002/098348 | 12/2002 |
| WO | 2002/102444 | 12/2002 |
| WO | 2003/000202 | 1/2003 |
| WO | 2003/022304 A1 | 3/2003 |
| WO | 2003/055547 A1 | 7/2003 |
| WO | 2003/057170 | 7/2003 |
| WO | 2003/061578 A2 | 7/2003 |
| WO | 2003/072195 A2 | 9/2003 |
| WO | 2003/080149 A2 | 10/2003 |
| WO | 2003/086345 | 10/2003 |
| WO | 2003/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |

(56) References Cited

FOREIGN PATENT DOCUMENTS

| | | |
|---|---|---|
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047281 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | 2011/017554 A2 | 2/2011 |
| WO | 2011/056889 A1 | 5/2011 |
| WO | 2011/163272 | 12/2011 |
| WO | 2012/064892 A1 | 5/2012 |
| WO | 2012/135765 | 10/2012 |
| WO | 2012/174472 A1 | 12/2012 |
| WO | 2012/174556 A1 | 12/2012 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/0144895 A1 | 9/2014 |
| WO | 2015/010092 A1 | 1/2015 |
| WO | 2015/021064 A1 | 2/2015 |
| WO | 2015/148905 A1 | 10/2015 |

OTHER PUBLICATIONS

Fadl et al., Effects of MDI spray angle on aerosol penetration efficiency through an oral airway cast. Journal of Aerosol Science, vol. 38, No. 8, pp. 853-864 (2007).

Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).

Farr, S.J. et al., Pulmonary insulin administration using the AERx® system:physiological and physiochemical factors nfluencing insulin effectiveness in healthy fasting subjects. Diabetes Tech. Ther. 2:185-197, 2000.

Fehmann et al. "Cell and molecular biology of the incretin hormones glucagon-like peptide-1 and glucose-dependent insulin releasing polypeptide." Endocrine Reviews 16:390, 1995.

Ferrin et al, Pulmonary retention of ultrafine and fine particles in rats. Am. J. Repir. Cell Mol. Biol., pp. 535-542 (1992).

Festa et al., "LDL particle size in relation to insulin, proinsulin, and insulin sensitivity" Diabetes Care, 22 (10):1688-1693 (1999).

Forst et al., "Metabolic Effects of Mealtime Insulin Lispro in Comparison to Glibenclamide in Early Type 2 Diabetes", Exp. Clin. Endocrinol. Diabetes, 2003, 111, 97-103.

Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.

Galinsky et al., A synthesis of diketopiperazine's using polyphosphoric acid. Journal of the American Pharmaceutical Association, vol. 46, No. 7, pp. 391-393 (1957).

Garber, "Premixed insulin analogues for the treatment of diabetes mellitus", Drugs, 66(1):31-49 (2006).

Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.

Garg SK, Kelly W, Freson B, et al. Treat-to-target Technosphere® insulin in patients with type 1 diabetes. ADA 2011; Abstract 941-P.

Garg SK, McGill JB, Rosenstock J, et al. Technosphere® insulin vs insulin lispro in patients with type 1 diabetes using multiple daily injections. ADA, Abstract 917-P (2011).

Gates BJ "Update on advances in alternative insulin therapy." Advances in Pharmacy 1:159-168, 2003.

Glucagon for Injection (1999) glucagon for injection (rDNA origin), pp. 1-7.

Glucagon-like peptide-1; http://en.wikipedia.org/wiki/Glucagon-like peptide-1 (accessed Apr. 24, 2015).

Glucophage Product Insert. Jan. 2009.

Glucotrol Product Insert. Sep. 2006.

Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).

Goke et al., Exendin-4 is a high potency agonist and truncated exendin-(9-39)-amide an antagonist at the glucagon-ike peptide 1-(7-36)-amide receptor of insulin-secreting beta-cells. J. Biol. Chem. 268(26):19650-19655 (1993).

Golpon et al. "Vasorelaxant effect of glucagon-like peptide-(7-36) amide and amylin on the pulmonary circulation of the rat." Regulatory Peptides 102:81, 2001.

(56) References Cited

OTHER PUBLICATIONS

Gonzalez et al., Actualizacion del tratamiento farmacologico de la diabetes mellitus tipo 2. Del Sistema Nacional de Salud vol. 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al. "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab , 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 34, pp. 373-379 (2007).
Orgsoltab et al., Division of Organic Chemistry. Ohio Northern University. Nov. 24, 2009. Available from <http://www.2.onu.edu/~b-meyers/organic_solvents.html>.

(56) References Cited

OTHER PUBLICATIONS

Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Dbesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Dpin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist. com, Decision News Media SAS (2006).
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with nhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157,2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86:1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.

(56) References Cited

OTHER PUBLICATIONS

Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells". Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying J. Gene Medicine 2002; 4:428-437.
Shah et al. "Lack of suppression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulation in the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh et al., Use of 125l-[Y39]exendin-4 to characterize exendin receptors on dispersed pancreatic acini and gastric chief cells from guinea pig. Regul. Pept. 53 : 47-59 (1994).
Simms Jr, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007." Diabetes Tecnology & Therapeutics, vol. 9, Supplement 1, pp. S1-S3 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed by Examiner on May 16, 2014 in Non-Final Orfice Action dated May 22, 2014 for U.S. Appl. No. 12/883,369 in Non-Final Office Action dated May 22, 2014 for U.S. Appl. No. 12/883,369.
Shields, Irritable bowel syndrome, archived Jun. 21, 2009, available at: https://web.archive.org/web/200906211 00502/http://www.gastroenterologistpaloalto.com/conditions-diseases-irritable-bowelsyndrome-palo-alto-ca. html; on Aug. 26, 2015 is U.S. Appl. No. 14/139,714.
Smith et al., Evaluation of novel aerosol formulations designed for mucosal vaccination against infleunza virus. Vacine, vol. 21, pp. 2805-2812 (2003).
U.S. Appl. No. 14/873,041, filed Oct. 1, 2015.
Design U.S. Appl. No. 29/504,212, filed Oct. 2, 2014.
U.S. Appl. No. 14/774,311, filed Sep. 10, 2015.
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust Definitions and Concepts [retrieved from internet by Examiner in European case on Sep. 22, 2015], <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
U.S. Appl. No. 14/863,136, filed Sep. 23, 2015.
U.S. Appl. No. 14/991,777, filed Jan. 8, 2016.
U.S. Appl. No. 14/971,785, filed Dec. 16, 2015.
U.S. Appl. No. 14/945,168, filed Nov. 18, 2015.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin." Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et al. Pulmonary delivery of Technosphere™/insulin: Increased bioefficacy and bioavailability in

(56) References Cited

OTHER PUBLICATIONS clinical trials using the PDC Medtone™ inhaler. Proceed Int'l Symp Control Rei Bioact Mater 2000; 27: 1000-1001.

Stowell et al. "Development of GLP-1 Technosphere(TM) powder: an inhaled GLP-1 product." Diabetes Technology Meeting, San Francisco, Oct. 2007.

Strack "Inhaled Human Insulin." Drugs of Today 2006,42 (4): 207-221.

Sturis et al., GLP-1 deriative liraglutide in rats with beta-cell deficiences: influence of metabolic state on beta-cell mass dynamics. British Journal of Pharmacology, 140 : 123-132 (2003).

Svartengren et al., Added External Resistance Reduces Oropharyngeal Deposition and Increases Lung Deposition of Aerosol Particles in Asthmatics. Am J. Respir. Crit. Care Med., vol. 152, pp. 32-37, 1995.

Sympatecs. Dry Dispersion for Laser Diffraction and Image Analysis, 2011. XP-002586530.

Leone-Bay et al., Innovation in drug delivery by inhalation. Ondrugdelivery, No. 7, pp. 4-8 (2010).

Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.

Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.

Tang-Christensen et al. "Central administration of GLP-1-(7-36) amide inhibits food and water intake in rats." Am J Physiol 271 (Regulatory Integrative Comp Physiol 40):R848, 1996.

Taylor et al. "Aerosols for macromolecule delivery. Design challenges and solutions." Am J Drug Deliv 2:143-155, 2004.

Teeter et al. "Dissociation of lung function changes with humoral immunity during inhaled human insulin therapy." Am J Resp Crit Care Med 173:1194, 2006.

Telko et al., Dry Powder Inhaler Formulation. Respiratory Care, Sep. 2005, vol. 50, No. 9, 1209-1227.

The American Diabetes Association "Insulin Administration" Diabetes Care, vol. 27, Supplement 1, S106-S109 (2004).

Gerber et al., Treatment satisfaction with inhaled insulin in patients with type 1 diabetes. Diabetes Care 24:1556-1559 (2001).

The Lancet. 1989, vol. 333, p. 1235-1236.

Thorens "Expression cloning of the pancreatic b-cell receptor for the gluco-incretin hormone glucagon-like peptide-1." PNAS 89:8641, 1992.

Thorens B et al. "Cloning and function expression of the human islet GLP-1 receptor: demonstration that exendin-4 is an agonist and exendin-(9-39) an antagonist of the receptor." Diabetes 42:1678, 1993.

Todd et al. "Glucagon-like peptide-1 (GLP-1: a trial of treatment in non-insulin-dependent diabetes mellitus." Eur J Clin Invest 27:533,1997.

Todd et al. Subcutaneous glucagon-like peptide-1 improves postprandial glucaemic control over a 3-week period in patients with early type 2 diabetes. Clinical Science 95:325,1998.

Toft-Nielson et al. "Determinants of the effectiveness of glucagon-like peptide-1 in type 2 diabetes." J Clin Endocrinol Metab 86:3853, 2001.

Toft-Nielson et al. "Exaggerated secretion of glucagon-like peptide-1 (GLP-1) could cause reactive hypoglcaemia." Diabetologia 41:1180, 1998.

Toft-Nielson et al. "The effect of glucagon-like peptide-1 (GLP-1) on glucose elimination in healthy subjects depends on the pancreatic glucoregulatory hormones." Diabetes 45:552, 1996.

Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.

Triantafyllidis et al., Structural, compositional and acidic characteristics of nanosized amorphous or partially crystalline ZSM-5 zeolite based materials Microporous and Mesoporous Materials, 75:89-100 (2004).

Tu N, Kramer DA, Baughman RA. Inhaled Technosphere® Insulin improves glycemic control without weight gain. Diabetes 2007;56:Abstract 471-P.

Tuley et al., Experimental observations of dry powder inhaler dose fluidisation. International Journal of Pharmaceutics, 358, pp. 238-247 (2007).

Utah Valley University. Saponification. © 2009. Available from: <http://science.uvu.edu/ochem/index.php/alphabetical/s-t/saponification/printpage/>.

Vaczek, Accelerating drug delivery firms exploring new drug-delivery routes and devices intently awaiting the commercial launch of Exubera. Pharmaceutical & Medical Packaging News, vol. 14, No. 6 (2006).

Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.

Van Alfen-Van Der Velden et al. "Successful treatment of severe subcutaneou insulin resistance with inhaled nsulin therapy", Pediatric Diabetes 2010: 11:380-382.

Vara E et al. "Glucagon-like peptide-1 (7-36) amide stimulates surfactant secretion in human type II pneumocytes." Am J Resp Crit Care Med 163:840-846, 2001.

Vella A et al. "Effect of glucagon-like peptide 1(7-36) amide on glucose effectiveness and insulin action in people with type 2 diabetes." Diabetes 49:611, 2000.

Vella A et al. "The gastrointestinal tract and glucose tolerance." Curr Opin Clin Nutr Metab Care 7:479, 2004.

Vendrame et al. "Prediabetes: prediction and prevention trials." Endocrinol Metab Clin N Am, 2004, vol. 33, pp. 75-92.

Verdich C, et al., A meta-analysis of the effect of glucagon-like peptide-1 (7-36) amide on ad libitum energy intake in humans. J Clin Endocrinol Metab., 86:4382-4389, 2001.

Vilsboll et al. "Reduced postprandial concentrations of intact biologically active glucagon-like peptide-1 in type 2 diabetic patients." Diabetes 50:609, 2001.

Vilsboll et al. "Similar elimination rates of glucagon-like peptide-1 in obese type 2 diabetic patients and healthy subjects." J Clin Endocrinol Metab 88:220, 2003.

Vilsboll et al., "Evaluation of β-Cell Secretary Capacity Using Glucagon-Like Peptide 1", Diabetes Care, vol. 23, No. 6, pp. 807-812, Jun. 2000.

Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.

Heine "Unlocking the opportunity of tight glycaemic control. Promise ahead: the role of inhaled insulin in clinical practice." Diabetes, Obesity and Metabolism 7:S19, 2005.

Heinemann "Variability of Insulin Absorption and Insulin Action." Diabetes Technology & Therapeutics, vol. 4, No. 5, pp. 673-682. 2002.

Heinemann et al. "Current status of the development of inhaled insulin." Br. J. Diabetes Vasc. Dis. 4:295-301, 2004.

Heinemann L et al. "Time-action profile of inhaled insulin." Diabetic Med 14:63-72, 1997.

Heinemann, L. "Intra-individual Variability of the Metabolic Effect of Inhales Insulin Together with an Absorption Enhancer", Diabetes Care, vol. 23, No. 9, Sep. 2000, p. 1343-1347.

Heise et al. "The effect of insulin antibodies on the metabolic action of inhaled and subcutaneous insulin." Diabetes Care 28:2161, 2005.

Herbst et al., Insulin Strategies for Primary Care Providers. Clinical Diabetes, vol. 20, No. 1, pp. 11-17 (2002).

Heubner et al. "On inhalation of insulin" Klinische Wochenschrift 16:2342, 1924. (Original and English translation provided in one document).

Heyder "Particle Transport onto Human Airway Surfaces", Eur. J. Respir. Dis, Suppl. 119, 29-50 (1982).

(56) References Cited

OTHER PUBLICATIONS

Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R,Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESA® (inhaled Technosphere® insulin) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.

Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. Accessed by Examiner on Apr. 30, 2014 in Non-Final Offfice Action dated May 22, 2014 for U.S. Appl. No. 13/797,657, in Non-Final Office Action dated May 22, 2014 for U.S. Appl. No. 12/883,369.
International Search Report for PCT International Application No. PCT/US2010/055323 filed on Nov. 3, 2010.
Written Opinion dated Jul. 1, 2013 for International Application No. PCT/US2013/032162 filed on Mar. 15, 2013.
International Search Report dated Jun. 21, 2010 for International Application No. PCT/US2010/027038 filed on Mar. 11, 2010.
Written Opinion for International Application No. PCT/US2011/060057 filed on Nov. 9, 2011.
International Search Report dated Mar. 18, 2013 for International Application No. PCT/US2012/061749 filed on Oct. 24, 2012.
International Search Report dated Jun. 20, 2012 for International Applicaion No. PCT/US2012/031695 filed on Mar. 30, 2012.
International Search Report dated Nov. 19, 2014 for International Application No. PCT/US2014/049817 filed on Aug. 5, 2014.
International Search Report for International Application No. PCT/US2010/020448 filed on Jan. 8, 2010.
International Search Report dated Mar. 11, 2010 for International Application No. PCT/US2009/069745 filed on Dec. 29, 2009.
International Search Report dated Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavord Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, p. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).

(56) References Cited

OTHER PUBLICATIONS

Combettes and Kargar, C, Newly Approved and Promising Antidiabetic Agents. Therapie, Jul.-Aug. 2007: 62 (4): 293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line], MannKind Technologies Website, posted in 2011, [retrieved on Jul. 30, 2012], Retrieved from the Internet <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action dated Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Dorwald, F.A. Side reactions in organic synthesis. Wiley, (2005).
Doyle et al. "Glucagon-like peptide-1." Recent Prog Horm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).

Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest., 95 :417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.

(56) References Cited

OTHER PUBLICATIONS

Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1 )-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11):4542-4546 (2007).
Yoshida et al., Absorption of insulin delivered to rabbit trachea using aerosol dosage form. J. Pharm. Sci. 68(5):670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96:233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action dated Mar. 26, 2015 in U.S. Appl. No. 13/942,482.
Definition of matrix from http://medical-dictionary.thefreedictionary.com/matrix, retrieved by the Examiner on Mar. 5, 2015 and cited in Office Action dated Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left column of p. 656).
Ely et al., Effervescent dry powder for respiratory drug delivery. European Journal of Pharmaceutics and Biopharmaceutics 65: 346-353 (2007).
European Search report for European Application 14192154.4 dated Mar. 19, 2015.
Extended European Search report for European Application 14187552.6 dated Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fluidized bed granulating system. J. Soc. Powder Technol., Japan, 41: 514-521 (2004).
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11 (S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.

(56) References Cited

OTHER PUBLICATIONS

Potocka E, Hovorka R, Baughman R, et al. Characterization of metabolism parameters following Technosphere® insulin and insulin Lispro. ADA 2010; Poster 1561.

Potocka E, Hovorka R, Baughman RA, et al. AFRESA™ supresses endogenous glucose production earlier than a rapid-acting analog (Lispro) and inhaled Exubera® ADA 2009; Oral 232.

Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).

Prabhu et al. "A study of factors controlling dissolution kinetic of zinc complexed protein suspensions in various ionic species", Int. J. Pharm. 217(1-2):71-8 (2001).

Laube et al., The lung as an alternative route for delivery for insulin in controlling postrprandial glucose levels in patients with diabetes. Chest, Preliminary Report 114 (6) : 1734-1739 (1998).

Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.

Quddusi et al. "Differential effects of acute and extended infusions of glucagon-like peptide-1 on first- and second-phase insulin secretion in diabetic and nondiabetic humans." Diabetes Care 26:791, 2003.

Rachman et al. "Normalization of insulin responses to glucose by overnight infusion of glucagon-like peptide 1 (7-36) amide in patients with NIDDM." Diabetes 45:1524, 1996.

Raju et al., Naseseazines A and B: a new dimeric diketopiperazine framework from a marine-derived actinomycete, *Streptomyces* sp. Organic letters, vol. 11, No. 17, pp. 3862-3865 (2009).

Raskin et al. "Continuous subcutaneous insulin infusion and multiple daily injection therapy are equally effective in type 2 diabetes." Diabetes Care, vol. 26, No. 9, pp. 2598-2603, Sep. 2003.

Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.

Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.

Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.

Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).

Raufman et al., Truncated glucagon-like peptide-1 interacts with exendin receptors on dispersed acini from guina pig pancreas. J. Biol. Chem. 267(30): 21432-21437 (1992).

Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.

Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.

Rave et al. "Dose Response of Inhaled Dry-Powder Insulin and Dose Equivalence to Subcutaneous Insulin Lispro." Diabetes Care 28:2400-2405, 2005.

Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.

Rave et al. "Results of a Dose-Response Study with a New Pulmonary Insulin Formulation and Inhaler." Diabetes 49, Supplement, May 2000, A75.

Rave et al. "Time-action profile of inhaled insulin in comparison with subcutaneously injected insulin lispro and regular human insulin." Diabetes Care 28:1077, 2005.

Rave K, Heise T, Pfuetzner A, et al. Assessment of dose-response characteristics for a new pulmonary insulin formulation and inhaler. Exp Clin Endocrinol Diabetes 2000; 108:S161.

Rave K, Potocka E, Boss AH, et al. Pharmacokinetics and linear exposure of AFRESA™ compared with the subcutaneous injection of regular human insulin Diabetes, Obesity and Metabolism 2009; 11:715-720.

Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.

Razavi et al. "TRPVI+ sensory neurons control beta cell stress and islet inflammation in autoimmune disease." Cell 127:1123, 2006.

Retrieved from website: http://groups.molbiosci.northwestern.edu/holmgren/Glossary/Definitions/Def-P/placebo.html, 1 page. Retrieved on Mar. 12, 2013.

Rhodes et al. "Technosphere: Microspherical Particles from Substituted Diketopiperazines for Use in Oral Drug Delivery" 208th ACS National Meeting, Aug. 1994.

Richardson et al. "Technosphere Insulin Technology." Diabetes Technology & Therapeutics, vol. 9, Supplement 1, pp. S65-S72, 2007.

Richardson PC, Potocka E, Baughman RA, et al. Pharmacokinetics of Technosphere® insulin unchanged in patients with chronic obstructive pulmonary disease. Diabetologia 2009; 52 (suppl 1).

Richter et al. "Characterization of glucagon-like peptide-1(7-36)amide receptors of rat membranes by covalent cross-linking." FEBS Letters 280:247, 1991.

Richter et al. "Characterization of receptors for glucagon-like peptide-1 (7-36)amide on rat lung membranes." FEBS Letters 267:78, 1990.

Riddle "Combining Sulfonylureas and Other Oral Agents." Am J Med, 2000, vol. 108(6A), p. 15S-22S.

Riddle et al. "Emerging therapies mimicking the effects of amylin and glucagon-like peptide 1." Diabetes Care 29:435, 2006.

Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.

Rosen et al., Substance P microinjected into the periaqueductal gray matter induces antinociception and is released folloing morphine administration Brain Research, 1001: 87-94 (2004).

Rosenmund et al., Diketopiperazines from Leuchs Anhydrides. Angew Chern Intern. Edit. vol. , No. 2 (1970).

Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.

Johnson et al., "Turbuhaler a new device for dry powder terbutaline inhalation", Allergy 43(5):392-395 (1988).

Johnson et al: RyR2 and calpain-10 delineate a novel apoptosis pathway in pancreatic islets. J Biol Chem., 279(23):24794-802, 2004.

Johnson, Keith A., Preparation of peptide and protein powders for inhalation. Advanced Drug Delivery Reviews 1997; 26:3-15.

Jones et al., An investigation of the pulmonary absorption of insulin in the rat. Third European Congress of Biopharmaceutics and Pharmacokinetics, (1987).

Joseph et al. "Oral delivery of glucagon-like peptide-1 in a modified polymer preparation normalizes basal glycaemia in diabetic db/db mice" Diabetologia 43:1319-1328, 2000.

Joy et al. "Incretin mimetics as emerging treatments for type 2 diabetes." Annal Pharmacother 39:110, 2005.

(56) References Cited

OTHER PUBLICATIONS

Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted and Received 2007, published on web 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo" Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapters, pp. 43-56 (2001).
Labiris et al., Pulmonary drug delivery. Part I: Physiological factors affecting therapeutic effectiveness of aerosolized medications. British Journal of Clinical Pharmocology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere@/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. CurrOpin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.

(56) References Cited

OTHER PUBLICATIONS

Boer et al., Design and application of a new modular adapter for laser diffraction characterization of inhalation aerosols International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.
Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
BRAY "Exanatide" Am J Health-Sys Pharm 63:411, 2006.

Brownlee et al. "Glycemic variability: a hemoglobin A1c-independent risk factor for diabetic complications." JAMA 295:1707, 2006.
Bruce, D.G., et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. AFRESA® (Technosphere® insulin) dosage strengths are nterchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life" Considerations on shape and function. Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3):203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-467.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.

(56) References Cited

OTHER PUBLICATIONS

Amodeo et al., Pain peptides. Solution structure of orphanin FQ2. FEBS Letters, vol. 473, Issue 2, pp. 157-160 (2000).
Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).
Krondahl et al., Regional differences in bioavailability of an opioid tetrapeptide in vivo rats after administration to the respiratory tract. Peptides, vol. 23, No. 3, pp. 479-488 (2002).
Lee et al., Intrapulmonary potential of polyethylene glycol-modified glucagon-like peptide-1s as a type 2 anti-diabetic agent. Regulatory Peptides, 152:101-107 (2009).
Selam, Jean-Louis. Inhaled Insulin: Promises and Concerns. Journal of Diabetes Science and Technology, vol. 2, Issue 2, pp. 311-315 (2008).
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technosphere/Insulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67,1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
MannKind Corporation "Postprandial hyperglycemia: clinical significance, pathogenesis and treatment." MannKind Corporation Monograph. 2009.
MannKind Corporation, Pulmonary Delivery: Innovative Technologies Breathing New Life into Inhalable Therapeutics, www.ondrugdelivery.com, 2006.
Burcelin et al., Long-lasting antidiabetic effect of a dipeptidyl peptidase IV-resistant analong of glucagon-like peptide-1. Metabolism, vol. 48, No. 2, pp. 252-258 (1999).
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci, 45: 125-134 (1992).
Matsui et al. "Hyperplasia of type II pheumocytes in pulmonary lymphangioleiomyomatosis. Immunohistochemical and electron microscope study" Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia ndependently of gastric emptying and insulin secretion in humans." Am J Physiol Endocrinol Metab 290:E1118, 2006.
Mendes et al., A non-dimensional functional relationship for the fine particle fraction produced by dry powder nhalers, Aerosol Science 38, pp. 612-624 (2007).
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Moren, Aerosols in Medicine (2nd Ed.), Elsevier, pp. 321-350 (1993).

(56) References Cited

OTHER PUBLICATIONS

Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
International Search Report dated Nov. 21, 2013 for International Application No. PCT/US2013/057397 filed on Aug. 29, 2013.
Eavarone et al., A voxel-based monte carlo model of drug release from bulk eroding nanoparticles. Journal of Nanoscience and Nanotechnology, vol. 10, pp. 5903-5907 (2010).
Marino MT, Cassidy JP, Smutney CC, et al. Improvement in bioavailability of FDKP with the NexGen2A device: Implications for delivery of pulmonary insulin. Diabetes Technology Meeting 2009; poster.
"An inhaled insulin formulation (Technosphere Insulin) effectively improves glycaemic control in patients with type 2 diabetes mellitus." Inpharma Weekly, vol. 1522, Jan. 28, 2006, p. 8.
ACTOS Product Insert. Aug. 2008.
Adjusting Mealtime Insulin Doses. BD Diabetes. http://www.bd.com/diabetes/page.aspx?cat=7001&id=7280 (2014).
Ahren "GLP-1 and extra-islet effects." Horm. Med Res 36:842, 2004.
Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine; vol. 101, No. 11, p. 2395-2401 (2007).
American Diabetes Association, "Standards of medical care in diabetes—2009", Diabetes Care, Jan. 2009, 32 Suppl 1:S13-61.
Amin N, Boss AH, Petrucci R, et al. Pulmonary functions (over 2 years) in diabetic subjects treated with AFRESA® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.
Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.

Angelo et al., Technosphere Insulin: Defining the Role of Technosphere Particles at the Celluar Level. J. Diabetes Sci. Technol., vol. 3, Issue 3, pp. 545-554 (2009).
Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin ispro at meal-times" 2005 Diabetes UK, Diabetic Medicine, 23, 46-52.
Atherton, F. et al. "Synthesis of 2(R)-A3(S)-Acylamino-2-OXO-1-Azetidinyloxy U-Acetic Acids." Tetrahedron, vol. 10, No. 6, Jan. 1, 1984, pp. 1039-1046.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled iuman insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.

(56) References Cited

OTHER PUBLICATIONS

Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulinmew technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73:1721-1724 (1984).
Benito E et al. "Glucagon-ike peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier. Science 156: 1204-1206 (1967).
Berge et al., "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.

\* cited by examiner

FIG. 7

INSUFFLATION APPARATUS AND METHODS

CROSS REFERENCE TO RELATED APPLICATIONS

This application is a national phase filing of International Application Number PCT/US2014/049817, filed Aug. 5, 2014, which claims the benefit of U.S. provisional patent application No. 61/862,484, filed Aug. 5, 2013, the entire disclosures each of which are incorporated herein by reference.

TECHNICAL FIELD

The present disclosure relates to a drug delivery system, including an insufflation apparatus and methods for delivering a consistent powder discharge to an animal's lungs during inhalation cycles. In particular, the apparatus is configured with an automated computerized system which can be used to deliver drugs by insufflation, for example, to experimental animals for local and/or systemic drug administration studies. The apparatus achieves drug delivery with consistency and reproducibly.

All references cited in this specification, and their references, are incorporated by reference herein in their entirety where appropriate for teachings of additional or alternative details, features, and/or technical background.

BACKGROUND

The pulmonary route of administration is useful for delivering medicines into the lungs for treatment of local conditions or to achieve systemic absorption. For local treatments, the medicine can be delivered directly to the site of need where the compound can exert effect. Most current drugs delivered to the lungs are designed to have an effect on the tissue of the lungs. Examples of drugs for lung delivery include, vasodilators, surfactants, chemotherapeutic agents, or vaccines for flu, or other respiratory illnesses for the treatment of diseases, including, asthma, COPD, cystic fibrosis, and pulmonary infections. Pulmonary administration enables rapid treatment of these chronic and acute conditions. Drug formulations for treating pulmonary diseases such as asthma are available by several methods, including, using nebulizers such as treatment with PULMOZYME®, using metered-dose inhalers such as SYMBICORT®, and dry powder inhalers such as ADVAIR DISKUS®, PULMICORT FLEXHALER®. Other types of treatments, including biologics such as nucleotides drugs in genetic therapy have been delivered to the lungs, for example, for gene therapy of cystic fibrosis, where retroviral vectors expressing an effective adenosine deaminase are administered to the lungs.

Currently, formulations for treating systemic disease using biologic products are available primarily through injectable compositions. Dry powder compositions for pulmonary inhalation and systemic delivery of insulin have been used, including EXUBERA®, and AFREZZA®.

In cases where systemic absorption is desired, the large surface area of the lung, its thin wall structure, and its local proximity to the systemic circulation are beneficial. Drug delivery to the lungs provides advantages over oral administration of active agents such as proteins and peptides, which are sensitive to enzymatic deactivation or degradation in the gut. In addition, absorption through the lungs into the systemic circulation is more effective in reaching target tissues, bypassing the liver, which is the site of metabolic action of most drugs delivered by injections and other routes of administration. The potential for delivering many other compounds through the lungs for systemic administration, ranging from peptides and proteins to small molecules often requires numerous studies and approaches depending on the delivery system used.

For pulmonary delivery, medicines are often formulated into a liquid or dry powder format so that they can be aerosolized and inhaled by patients. Aerosolization is achieved by delivery devices such as inhalers, atomizers, and nebulizers, which convert a payload of the liquid or dry powder formulation into a respirable dispersion. The dispersion is comprised of particles suitably small for navigating the airway and depositing in the lung. Particles that are too large carry excessive inertia, impact the back of the throat, and are swallowed. Particles that are too small can be exhaled and never deposit in the lung.

Early development work on drug formulations often requires non-clinical testing. This may involve small animals, including, mice, rats and other rodents, wherein drug delivery, exposure and the resulting effects can be studied before progressing to large animals and into human administration studies. Pharmacokinetic and pharmacodynamic effects along with adverse events can be assessed using an animal model to help progress or halt development of candidate drug formulations. It is therefore, extremely important in evaluating a potential drug that the delivery of the formulation being tested is consistent to ascertain with more accuracy the envisioned delivery in humans. For example, if the drug is intended for delivery in a single inhalation using an inhaler together with a dry powder formulation, then the small animal testing should approximate the envisioned approach in humans.

Current model methodologies used to assess delivery and efficacy of drugs for pulmonary delivery, include liquid instillation or dry powder insufflation. These methods have been developed by researchers to enable placement of candidate drug formulations directly into the lung. The methods involve syringe-like systems such as the PennCentury DP-4, wherein an elongated blunted cannula, dry powder chamber and syringe are used to disperse the contents of the chamber into the animal's lungs. To perform the insufflation, the animal is lightly anesthetized and intubated to insert the device cannula past the vocal cords and into the trachea just before the carina, the tracheal bifurcation leading into the bronchi. Oftentimes, a laryngoscope is used to help the researcher guide the cannula during the insertion step. The syringe barrel is then depressed forcing the contents, either liquid, suspension, or powder out of the chamber, down the cannula, and into the animal's lung. The air volume to discharge the powder from an insufflator is typically between 1.0 to 5.0 mL depending on the animal species. Using this equipment, a valve feature within the powder chamber prevents air flow and the subsequent aerosolization until a minimum threshold pressure is achieved. Accordingly, researchers exert significant manual force to depress the syringe plunger during activation thereby aerosolizing the contents of the chamber with minimal air volume.

Two major challenges are encountered with the aforementioned techniques. The first challenge is one of timing delivery of the drug during the breathing cycle. Discharge of powder into an animal during exhalation results in sub-optimal delivery as the contents can be blown back and are not delivered to the test subject. With powder delivery, powder blow back condition results in exhalation of drug, making it impossible to estimate the magnitude of drug delivery and confounding any measurable effects by the drug. Manual discharge of powder or liquid to avoid blow back is difficult in animals with high respiratory rates and or small lung capacity, for example, in mice having typically, 90 breaths per minute. The second challenge is repeatability and/or consistency. Current technology requires a minimum pressure to disperse a drug formulation. The devices allow for a range of pressures above that minimum which affect both the quality and consistency of the dispersion. Airflows occurring with the minimum required pressure may produce an aerosol discharge with large particle sizes that are not able to be inhaled deep into the lung. Large sizes are prevented from navigating deep into the lung because inertial forces become too large forcing the drug laden particles into the upper airway branches of the lung. Conversely, airflows occurring with higher applied pressures may produce aerosol discharges with far greater quality. Particle sizes within these emitted aerosols will likely be reduced and therefore will have a much greater likelihood of depositing deeper in the lung. The dependence of consistency on the applied syringe plunger pressure is also difficult to overcome. Instillation and/or insufflation studies typically involve multiple animals which can lead to variations in drug delivery from animal to animal if procedures are manually executed. Sources of variation in the drug delivery make assessment of drug effect more difficult to interpret.

Dosing reproducibility during experiments requires that the drug formulation be delivered to the subject with consistent and reproducible results. Therefore, the inventors have seen the need to design and manufacture an apparatus, system, and method to overcome the problems encountered with standard apparatuses and procedures currently used.

SUMMARY

A drug delivery system is provided comprising an apparatus and a method for delivering a drug composition, including aerosolized particles to the lungs are disclosed.

The apparatus comprises devices configured for measuring and recording an animal's breathing cycles; ascertaining the intervals of the breathing cycles and delivering an aerosol at a predetermined interval relative to an animal's breathing, in particular during an inhalation. The apparatus can comprise one or more sensors selecting from a variety of sensors, including, but not limited to accelerometers, microphones, strain gauges and transducers.

In one embodiment, computer algorithms specific to the sensors can then characterize and quantitate the animal's breathing pattern and determine when to trigger the insufflation in order to synchronize delivery with a natural inhalation maneuver. In one embodiment, delivery of dose composition can also be synchronized with different portions of the breathing cycle prior to or during an inhalation. The duration of the inhalation can also be checked, and assessed to determine the extent of delivery relative to the start and end of the inhalation. In one embodiment, active monitoring of the animal's breathing also generates data on duration of inhale/exhale, regularity of breathing, and other characteristics of the breathing cycle. In this and other embodiments, the apparatus is provided with an automated driving mechanism that displaces air through the insufflation device, by adapting an electromechanical device. In one embodiment, a linear solenoid can be used to displace a driving pump's piston, which ensures repeatable driving force and results in repeatable discharge flow rates.

In one embodiment, an apparatus is provided comprising:

a first device comprising a platform comprising an area for positioning an animal and configured to hold an animal in place and comprising an adjustable strap adapted with at least one sensor which detects movement of distension of the animal's thorax and/or abdomen due to breathing; said sensor generates a signal and communicates the signal to a microprocessor for analysis; and mounting means, including a stand for securing to said platform;

a second device comprising a solenoid, a syringe pump and a powder reservoir; wherein said solenoid is actuated by an onboard relay output system to pressurize the syringe pump; said second device further comprising a computer interface comprising a programmable algorithm which detects an animal's breathing pattern and said solenoid is actuated to pressurize the syringe pump at a predetermined interval during an inhalation to release a powder plume from the powder reservoir.

In one embodiment, the first device can further comprise a second sensor, which can detect sound generated from the animal's breathing cycles. In this and other embodiments, the apparatus can also comprise one or more modules comprising a relay board for relaying an output signal, such as an automated on and off switch; and a data acquisition board. In this embodiment, a first sensor communicates a first set of input signals to a first microprocessor configured with a data acquisition board which captures the input signals from the sensors, processes and analyzes the first set of signals in the first device and continuously streams to a computer and communicates with a relay board to actuate the solenoid and pressurize the syringe to discharge a powder contained in the powder reservoir at a predetermined interval.

In one embodiment, the first device comprises an adjustable cantilevered arm on which a transducer is mounted and can be positioned in the desired position on an animal to best measure physiological changes associated with breathing, such as diaphragm distention.

In a particular embodiment, a drug delivery system is provided comprising: an air pump adapted with a solenoid; an insufflation or instillation device adaptable to said air pump and comprising a chamber for containing a drug composition and a cannula; one or more sensors which can detect signals from breathing cycles of an animal; and a data acquisition board comprising an executable algorithm analyzing and transmitting signals from said one or more sensors, wherein the executable algorithm contains instructions to actuate the solenoid at a predetermined interval of a breathing cycle of the animal. In an example embodiment, the acquisition board can process the signals from the sensors within a computer, which makes the system modular, or can be part of a microprocessor built-in with the solenoid. In one embodiment, the animal is anesthetized and the system can have at least two sensors, including an accelerometer and a microphone.

In further embodiments, a method for insufflating an animal, including for example dogs, cats, monkeys, and rodents such as a mouse or a rat is disclosed. In a particular embodiment, the method comprises: anesthetizing an animal; positioning one or more sensors on or near the animal in the insufflation apparatus; detecting and analyzing the animals breathing cycles and administering a dose of a test composition at the inhalation interval of said animal. In an alternate embodiment, the method can also be used to instill a solution, a suspension, and/or a vapor to an animal.

In a particular embodiment, detecting and analyzing the animal's breathing cycles comprises positioning one or more sensors, such as an accelerometer, a microphone, or a transducer on or near the animal, which sensor(s) can detect signals from the animal, and transmit the signals to a data acquisition board, through which signals are analyzed and evaluated using an algorithm executable by, for example, a microprocessor on board a computer, or a programmable logic controller (PLC).

In one embodiment, signals from one or multiple sensors including, but not limited to microphones, thermocouples, strain gauges, accelerometers, and the like are used to optimally position the sensor(s) relative to the animal. In this embodiment, positioning information is relayed via a computer interface in which an algorithm detects the sensor output. An algorithm determines if the position is acceptable using sensor specific criteria, for example, validity of signal to noise, peak detection, slope detection, baseline noise and the like. The positioning of the sensor can occur manually by an operator or automatically using computer controlled, including motors and pneumatics, and sensor feedback.

In one embodiment, the method comprises, positioning an animal to be tested to an accessible area, for example, strapping the animal to a platform comprising an adjustable belt comprising one or more sensor(s), including an accelerometer, a transducer and/or a microphone; positioning the one or more sensor(s) to detect one or more signals generating from the animal's breathing cycles; actuating a power source and setting the accelerometer to detect a predetermine number of input signals to characterize the breathing pattern of the animal; and delivering an aerosolized powder plume to the animal during an inhalation. In a specific embodiment, the method comprises, determining the animal's breathing rate and inhalation intervals; and delivering a dose of an aerosolized composition at an inhalation interval. In some embodiments, the animal can optionally be strapped to the platform comprising a restraining area. In some embodiments, the adjustable belt can comprise an elastic material.

BRIEF DESCRIPTION OF THE DRAWINGS

FIG. 7 is a computer screenshot showing an output signal from an embodiment apparatus which signal was obtained using a balloon connected to a pump (FIG. 6B setup) to simulate breathing by mimicking inflate and deflate such as during a breathing cycle for a small rodent and assembled into the device.

DETAILED DESCRIPTION

In embodiments disclosed herein, there is disclosed an apparatus, a system, and a method for delivering drugs to an animal by insufflation.

In an exemplary embodiment illustrated in FIGS. 1-7, there is disclosed an insufflation apparatus with an interactive system and methods for administering intratracheal aerosols to small animals, including mice and rats. The apparatus 10 can be used to deliver aerosols in dry powder, suspension, or in liquid form. In one embodiment, the apparatus 10 can be used to insufflate, for example, mice, or Sprague-Dawley rats with dry powder aerosols for delivering test drug formulations in research and development, and for use in small animal practice in veterinary medicine, including, dogs, cats, guinea pigs, hamsters, monkeys, and the like.

Figure 1:
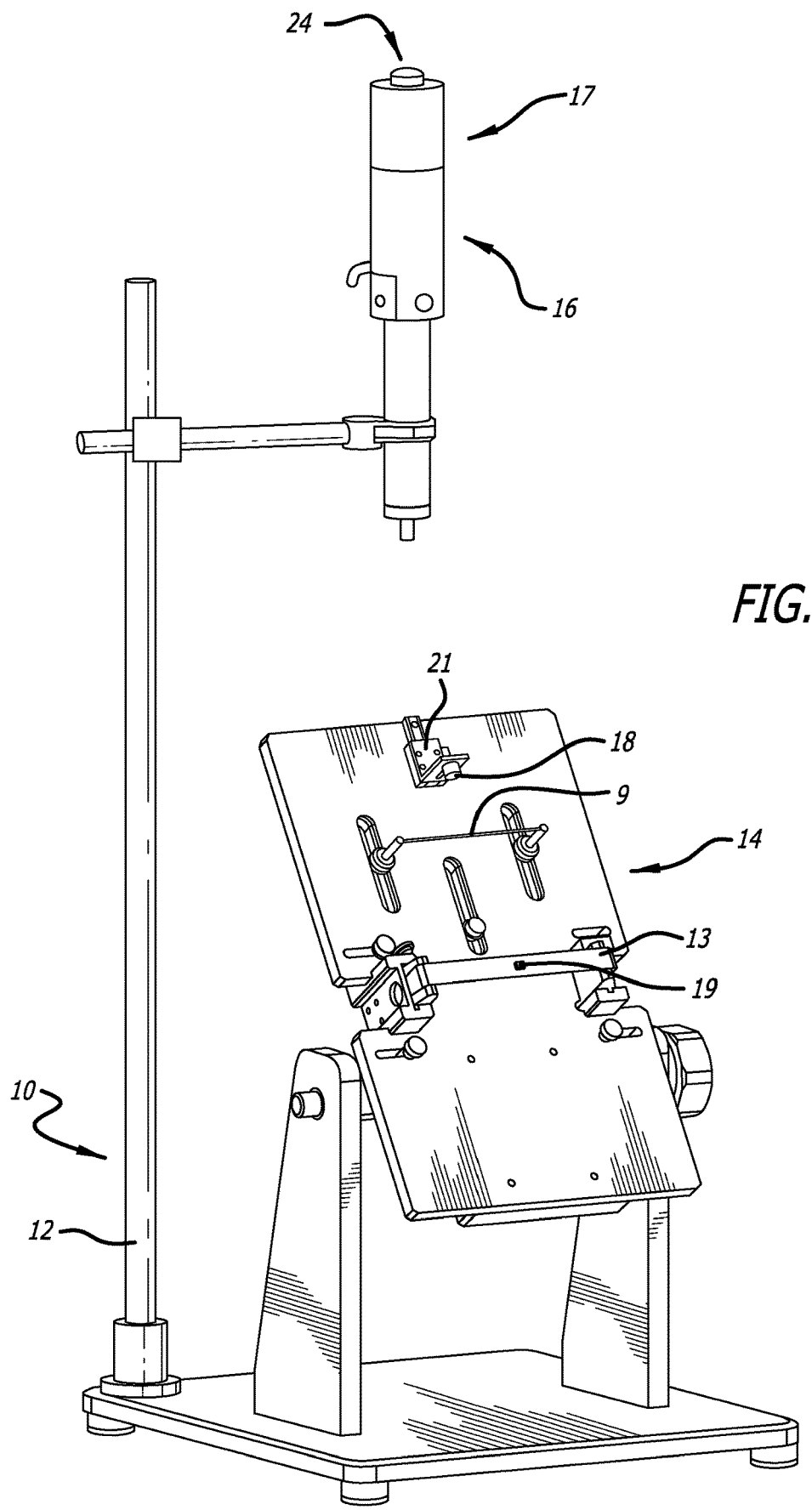
FIG. 1 depicts a schematic representation of an embodiment of the drug delivery system or apparatus.

In this embodiment and illustrated in FIG. 1, the insufflation apparatus 10 comprises a stand, a platform 14 (FIGS. 2A and 2B) for positioning an animal, including a mouse or a rat, a movable adjustable retainer 9, a data acquisition system (not shown), a strap 13 comprising a sensor 15 such as an accelerometer and/or microphone, a solenoid 17 adapted to a small volume air pump 16 (FIG. 3), and a unit-dose reusable insufflation device (FIG. 5) to disperse pre-metered masses of powder from a powder reservoir adapted with a cannula 28. In this embodiment, the apparatus comprises a sensor 18 such as microphone and an accelerometer 19 to monitor breathing signals, including, sound signals, air flow, chest or diaphragm distention signals, and the like. In some embodiments, the apparatus may comprise a single sensor or multiple sensors, which can be used to detect different types of signals from the animal and include, but are not limited to, transducers, strain gauges, pressure gauges, or thermistors.

Figure 4:
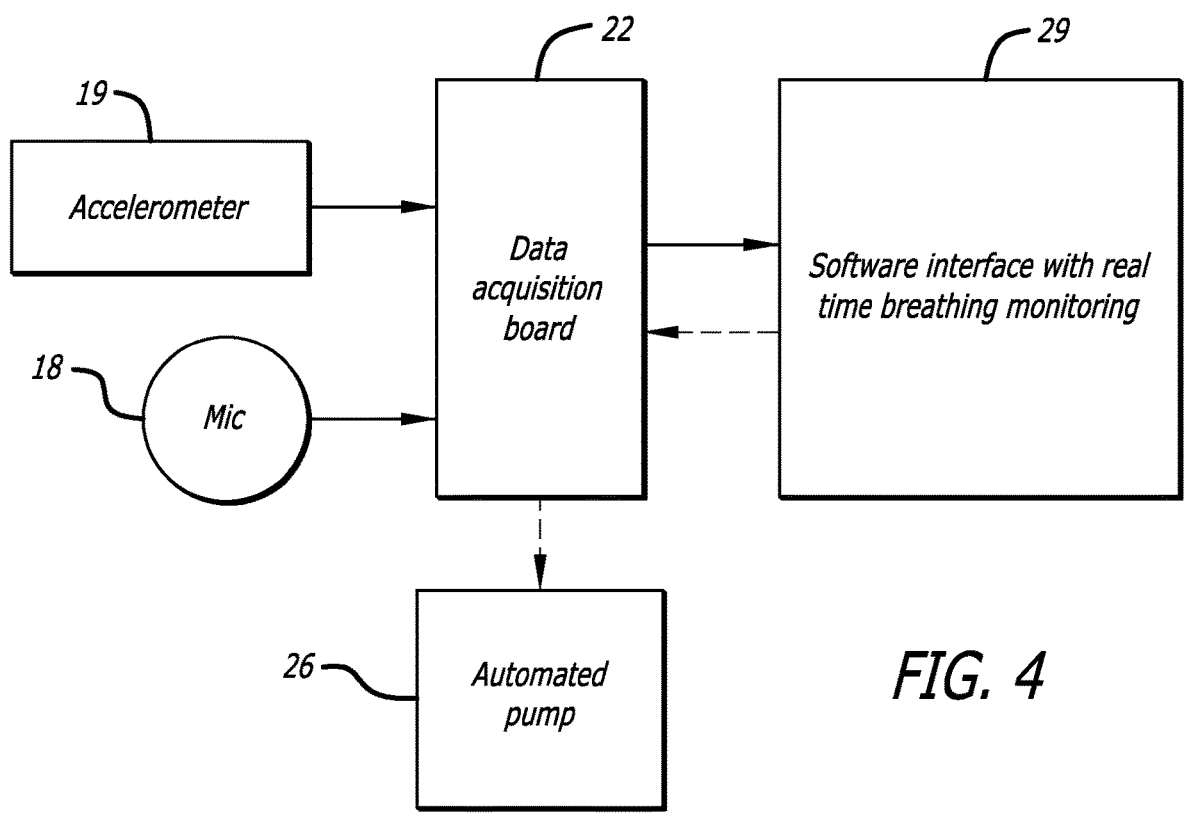
FIG. 4 depicts a schematic representation of an embodiment herewith depicting a flow chart illustrating the functional systems associated with the apparatus of FIG. 1.

FIG. 4 is a schematic representation of an embodiment herewith, and illustrates an example of the physical and/or electronic interactions between various components of apparatus 10, wherein apparatus 10 comprises two sensors, a first sensor which can be an accelerometer 19 for detecting distension of the abdomen, and a second sensor, for example, a miniature microphone 19 for detecting breathing sounds generated from the breathing cycles of an animal. In this embodiment, both types of signals generated from the first sensor 18 and second sensor 19 are relayed to a data acquisition board 22, which receives the different types of signals and streams them to a software interface comprising real-time breathing monitoring analysis and processing capabilities of an animal's breathing cycles. Apparatus 10 is controlled with software algorithms to correlate characteristic electrical signals from the sensors to the animal's breathing. FIG. 4 also shows that output signals from data acquisition board 22 are sent to an automated pump controller 26 to actuate solenoid 17 adapted to syringe pump 16 to automatically actuate the solenoid when an insufflation maneuver is needed to administer a dose during a test or treatment procedure.

In this and other embodiments, the actuation of the air pump 16 by solenoid 17 can also be controlled to exert constant or varying force levels based on selection of hardware and software algorithm features. In one embodiment, the trigger of the automated air pump 16 is controlled by an executable algorithm and can then be actuated at any point in the breathing cycle. This will allow for triggering of the pump offset from a feature within the breathing cycle or in a manner predictive of inhale, exhale, or other marker in the breathing cycle. In this embodiment, the optimal actuation is expected to be upon start of an animal's inhalation period. In one embodiment, aerosol delivery will occur in a single or multiple short bursts and during a single, or multiple consecutive, or non-consecutive inhalations depending on the dose and the animal.

In an exemplary embodiment as disclosed in FIGS. 1 through 5, FIG. 1 illustrates an animal stand 12, 14, and a solenoid 17 driven hand pump 16. FIG. 2 provides a close-up of the animal stand pictured in FIG. 1 comprising: platform 14, an animal retaining adjustable bar device 9 and animal strap 13 comprising sensor 19. In this particular embodiment, animal stand 14 comprises a microphone slide 20 and bracket 21, microphone 18, hanging wire and neck support post 9, adjustable strap 13 mounts and the strap with accelerometer 19 mounted to it. In this embodiment, the rat is meant to hang from wire 9 by its incisors, and the neck post provides support and alignment for the rear of the animal's neck. The strap 13 and accelerometer 19 are designed to be positioned over the diaphragm on the chest-abdomen area to detect the animal's breathing cycles. Microphone 18 is positioned near the animal's nose, to be able to monitor its breathing cycles. Data is collected from microphone 18 and accelerometer 19 by analog ports on data acquisition board 22, and an executable algorithm is run which converts both the accelerometer and microphone signals into information describing the animal's breathing pattern.

Figure 2A:
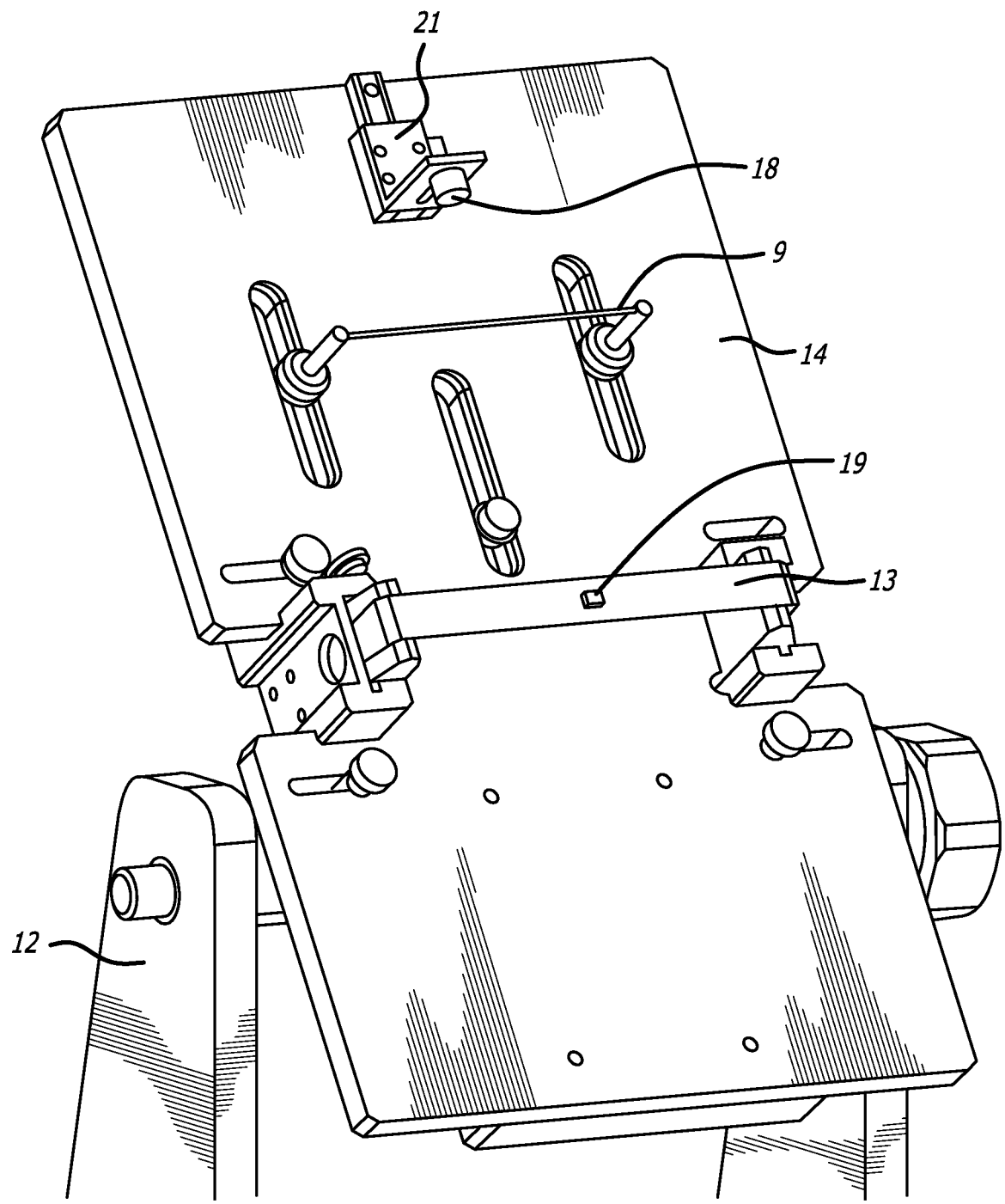
FIG. 2A depicts a schematic representation of the apparatus embodiment of FIG. 1, illustrating the details of a platform embodiment adapted with a strap containing an accelerometer for positioning on an animal.
Figure 2B:
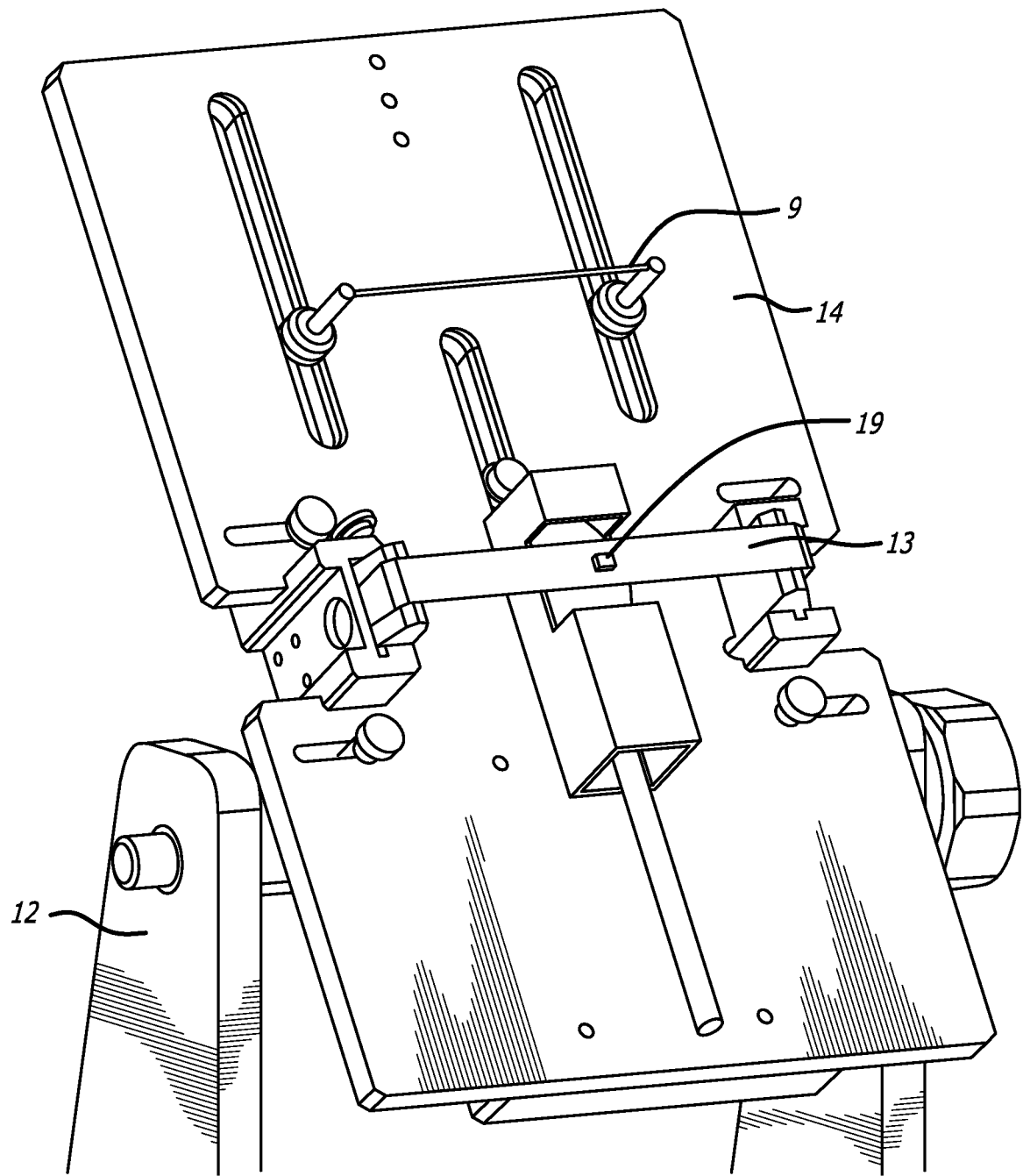
FIG. 2B depicts FIG. 2A showing a balloon mouse simulator adapted to the apparatus for in vitro testing studies.

FIG. 2B is the embodiment of FIG. 2A comprising an adaptor for in vitro studies of the insufflation apparatus and comprising a balloon positioned in the center of the adaptor and connected to an air pump which inflates the balloon at predetermine intervals to simulate breathing patterns of a small animal. In one embodiment, the air pump is automatically controlled by a computer program.

Figure 3:
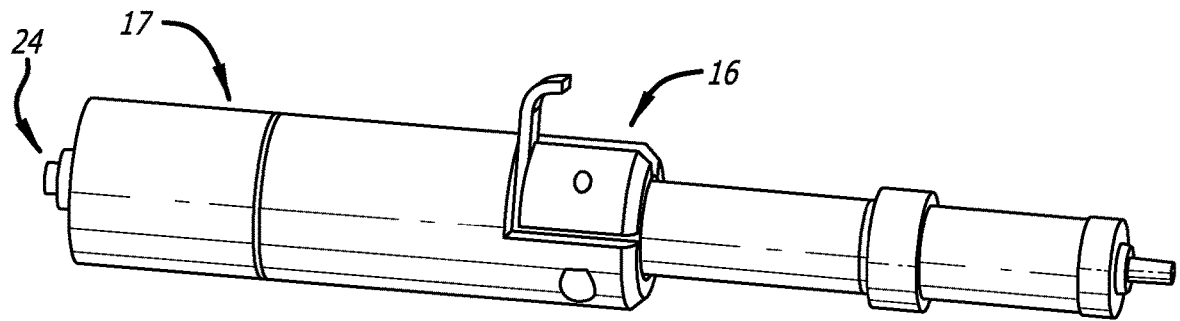
FIG. 3 depicts a schematic representation of an embodiment device component of the apparatus of FIG. 1 showing a solenoid and syringe pump system.

FIG. 3 is a drawing of an embodiment, which provides a close-up or more detailed view of the automated pump embodiment in FIG. 1. The automated air pump assembly 16 comprises an adjustable spring return hand pump, a solenoid mounting cylinder 17 and a solenoid 24. In one embodiment, the discharge volume of hand pump 16 can be adjusted to volumes less than the animal's regular or tidal breathing volume to reduce over-pressurizing the animal's lung during an insufflation procedure. For a small animal, the air pump can discharge volumes less than 5 ml, less than 3 ml, less than 2 ml, or less than 1 ml, depending on the animal to be insufflated. In one embodiment, the volume of pressurized air delivered by syringe pump 16 is from about 0.25 ml to about 1.5 ml, or from about 1 to 1.5 ml. In some embodiments, larger volumes greater than 3 ml of air can be delivered depending on the animal and the size of the dose to be administered. In one embodiment, the syringe pump is driven by solenoid assembly, which generates results in a repeatable manner and consistent force profile, since force is applied in a consistent manner. The automated air pump assembly in use provides a reduction in air volume required in typical insufflators to deliver the contents of a dose from the insufflation device, thus limiting dose content blow back post insufflation.

FIG. 4 specifically depicts a block diagram showing the sequence required for automation. In this embodiment, the apparatus 10 can be activated by pushing the run button on the software interface. The actuation trigger of apparatus 10 begins the collection of signals from both the accelerometer 19 and microphone 18. The analog signal from accelerometer 19 is processed before data acquisition board 22. Analog signals from each sensor 18, 19 are transmitted to the data acquisition board 22, which then transmits the signals to the software in a computer or PLC for additional processing and real time analysis. Using the software set of instructions, the signals from each sensor 18 and 19 are converted into signals describing the breathing pattern of the animal with relevant parameters, for example, duration of inhale, duration of exhale, breaths per minute, change in breathing rate, tidal volume, and the like. The computer software 29 instructions enables the rapid identification of the start of the animal's inhalation maneuver, and thus allows for the actuation of the pump and discharge of the drug liquid, suspension or powder prior to the end of a single inhalation. In some embodiments, if the quantity of drug exceeds a volume that can be administered in one inhalation, it is possible to administer the drug by a predetermined number of consecutive inhalations, or at predetermine intervals that can skip one or more inhalations.

Figure 5:
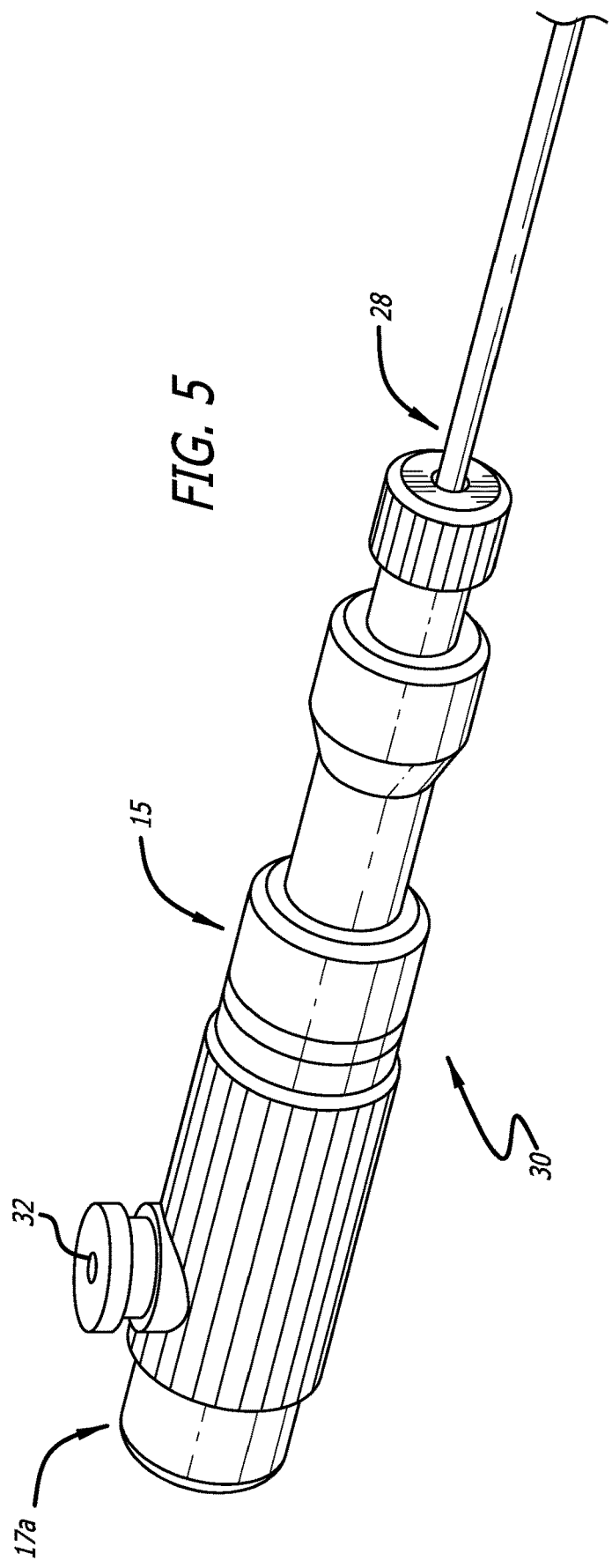
FIG. 5 depicts an embodiment of the insufflation device for adapting to the apparatus illustrated in FIG. 1 and containing a drug chamber or reservoir and showing a cannula for intubating an animal and delivering a powder dose.
Figure 6:
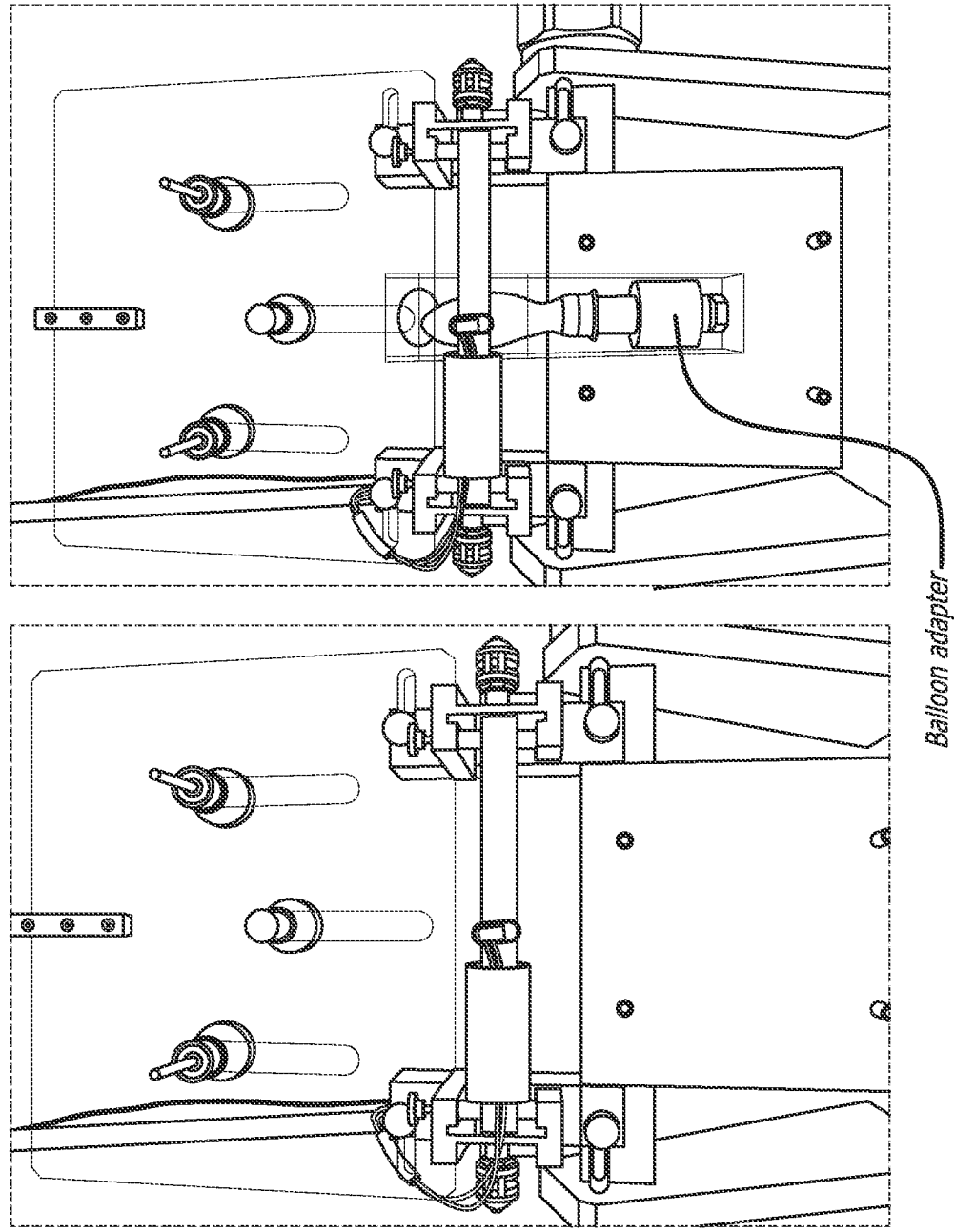
FIG. 6A is a photograph of platform section of the embodiment illustrated in FIG. 1 showing its components part and an attached balloon simulation adaptor is showing in FIG. 6B to represent a small animal.

As previously stated, the insufflation system can be used to administer liquids, suspensions and dry powders by intratracheal insufflation. FIG. 5 depicts an embodiment of a single dose reusable insufflation device 30, which can be adapted to apparatus 10 in series with air pump 16 for use with a small animal such as a rodent insufflation system. In this embodiment, the insufflation device 30 can be designed to administer various types of composition, including dry powders and comprises a substantially cylindrical body in the form of a syringe 30. In one embodiment, insufflation device 30 can connect to automated air pump 16 by a short tube 17a. The device can be made of materials, including metal to alleviate static effects on the drug composition being insufflated. The insufflation device 30 further comprises a chamber 15 with one or more valves for containing a powder composition. In alternate embodiments, the chamber 15 can comprise a reservoir for liquids or suspensions for use in instillations. The tip of the insufflation device 30 comprises a blunt cannula 28, which is used to directly intubate an anesthetized animal. Once the animal is intubated, the blunt end of the cannula is for positioning through the animal's mouth until it reaches near the carina of the tracheal region of the respiratory tract to ensure lung deposition of the drug composition to be insufflated. FIG. 5 also illustrates the insufflation device 30 further comprising an air inlet port 32 for allowing air into the pump upon retraction of the piston of the syringe pump 16; and one or more valves (not shown) to regulate air intake and powder containment in chamber 15 prior to delivery. Moreover, chamber 15 can be remove from the short tube 17*a* with or without cannula 28 to provide replacement of individual dosing units.

Figure 8:
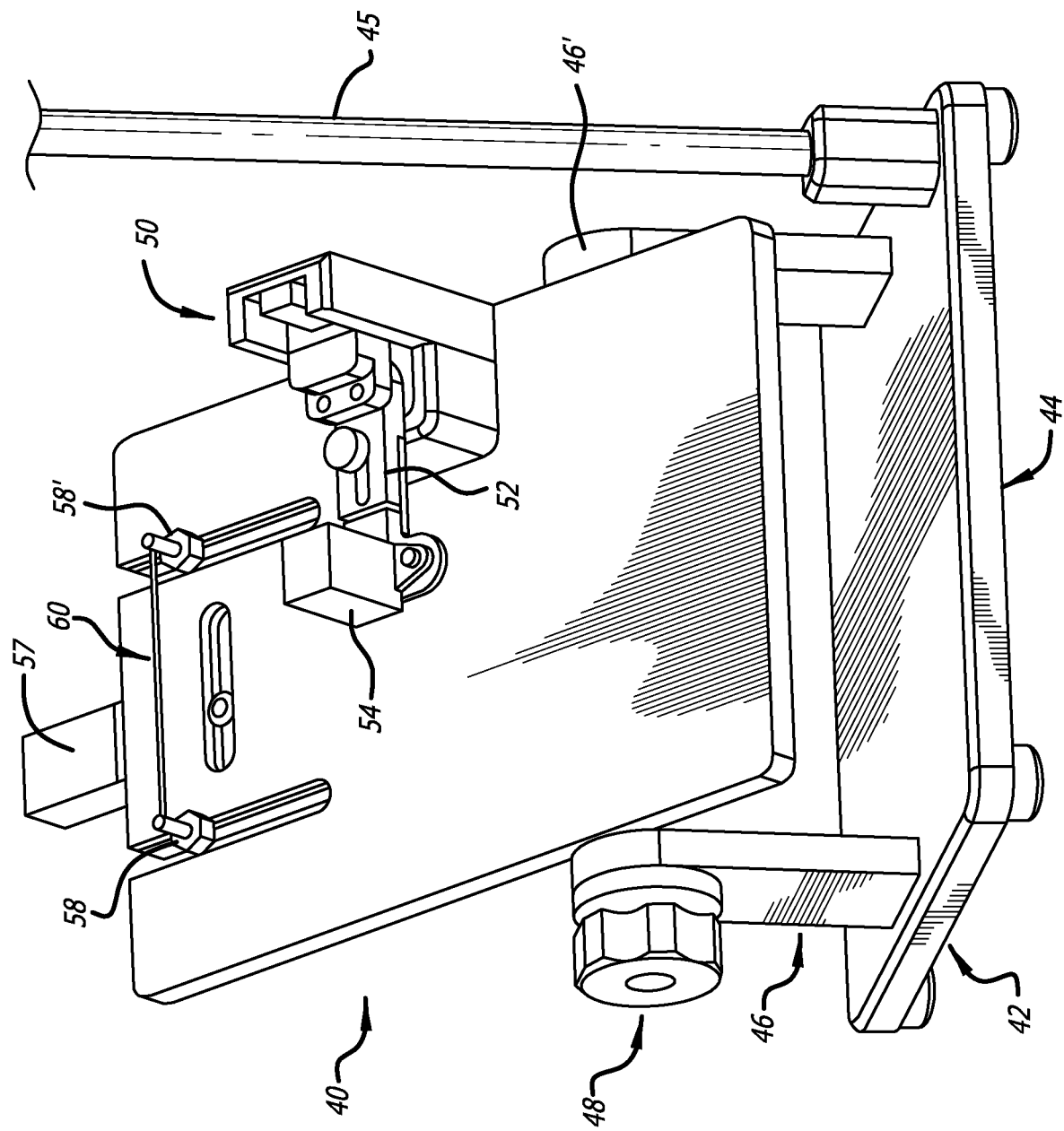
FIG. 8 is a schematic representation of an alternate platform embodiment of the apparatus embodiment of FIG. 1, depicting a movable cantilevered arm containing a linear positioning sensor for use with small experimental animals.
Figure 9:
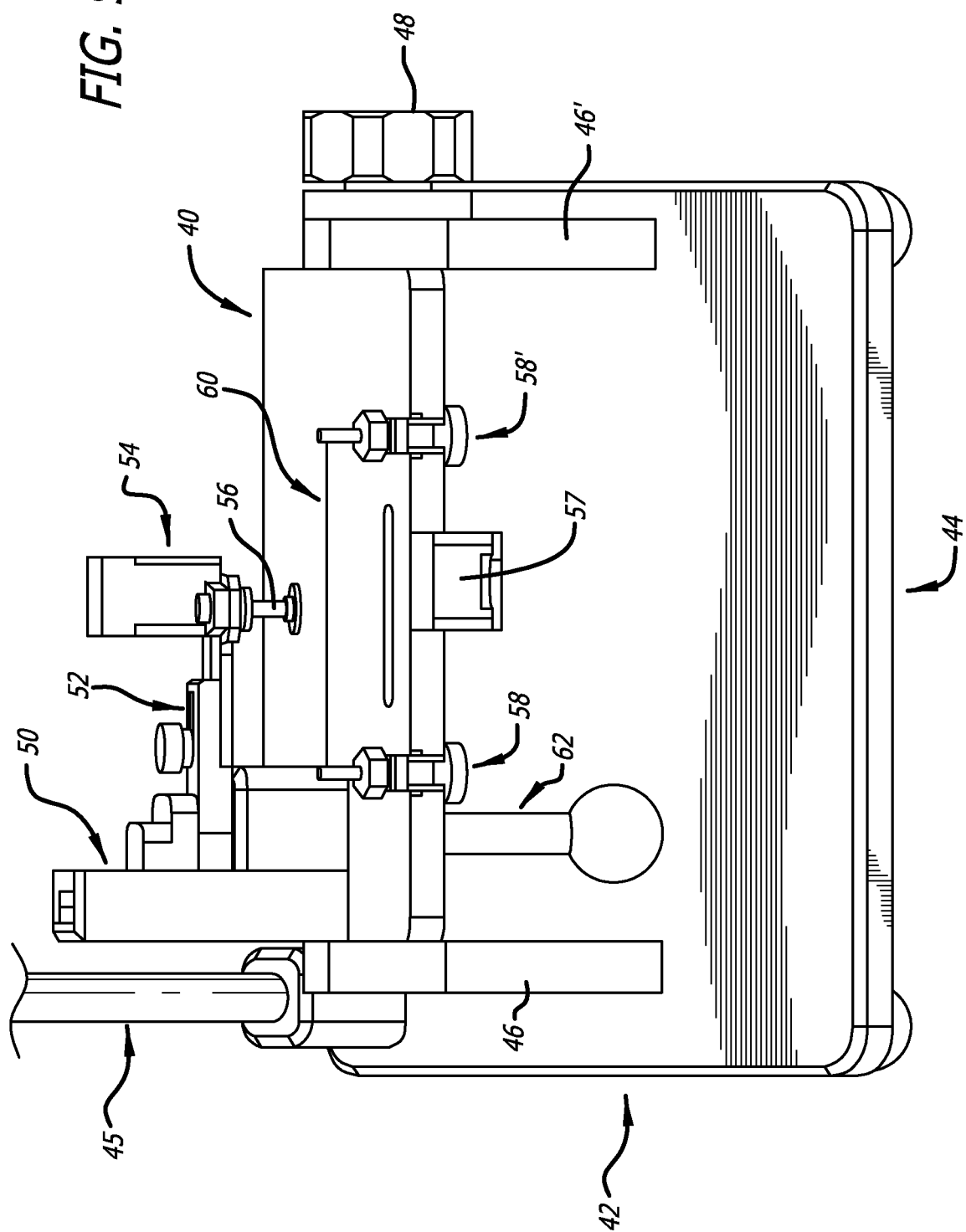
FIG. 9 is a schematic representation of a modified top view of the platform embodiment in FIG. 8 showing the positioning of the cantilever moveable on a stage.

In an alternate embodiment, the insufflation apparatus comprises a platform 40 for use with animals that may not need to be strapped or restrained. In this embodiment shown in FIGS. 8 and 9, platform 40 is mounted on a stand 42 comprising base 44, support beams 46, 46' adapted with hinge 48 configured to hold platform 40 and a shaft 45 to hold and support an air pump; solenoid and insufflation device. In this embodiment, platform 40 supported by a stand 43 configured on base 44 and it is designed to comprise an adjustable stage assembly 50 comprising a cantilevered arm 52 that can be moved to different positions depending on the size of the animal to be insufflated. In one embodiment, arm-like structure 52 is connected to platform 40 through a joint to pivot, rotate and or extend, and can be placed over the abdomen of the animal. FIG. 9 is a modified top view of a portion of the apparatus illustrated in FIG. 1 adapted with a platform as shown in FIGS. 8 and 9. As seen in FIGS. 8 and 9, sensor 54 comprises a transducer in particular, linear sensor pin 54, including, pin 56; wire posts 58, 58'; wire 60 for holding, for example, a rat by its incisor teeth; and screw 62 for adjusting or moving the stage to position and adjust the sensor on an animal. In this embodiment, screw 62 moves the cantilevered arm up and down on a vertical plane. In some embodiments, platform 40 can be adapted with a robotic arm comprising a plurality of sensors, including sensor 54, microphones, thermistors, transducers, or an accelerometer.

In some embodiments, platform 40 can further include a nose cone 57 that can removably attach to the top end of the platform. Nose cone 57 can serve as a mount allowing tubing to be passed through in order to keep an animal anesthetized.

In an alternate embodiment, the sensor on the cantilevered arm can comprise an accelerometer or other types of sensing device. The sensor 54 can be placed at the distal end of the arm for monitoring breathing signals from the animal. FIG. 8 depicts an embodiment with the swivel arm-like component of the insufflation apparatus. In an alternate embodiment, platform 40 comprises a robotic arm comprising an accelerometer.

Figure 10:
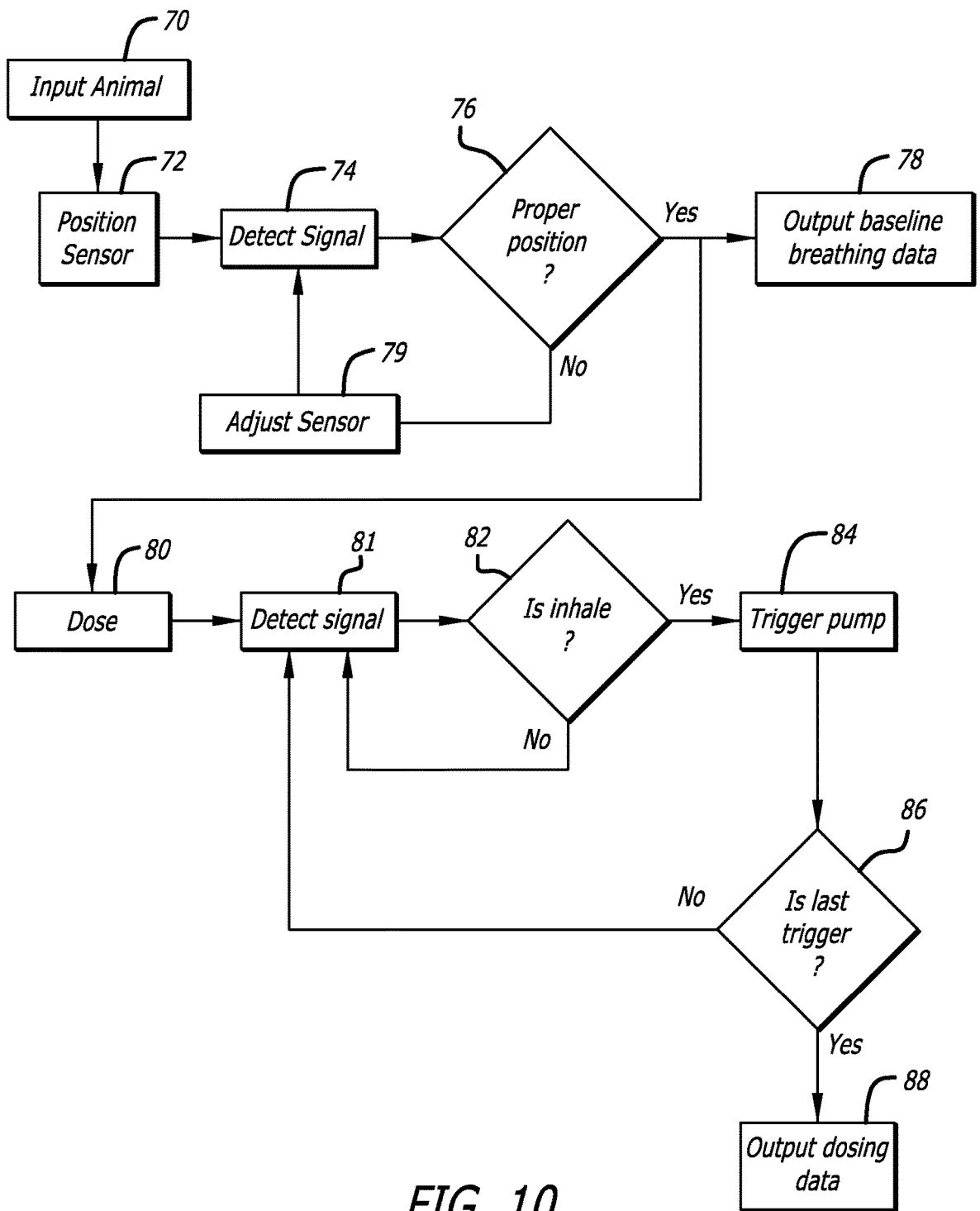
FIG. 10 is schematic representation of the functional components of the operating system of the drug delivery apparatus.

FIG. 10 is schematic representation of the functional components of one operating system of the drug delivery apparatus. As indicated in FIG. 10, input signal 70 generated from an animal is detected by sensor 74 once the program has been initiated to position the sensor 72. This signal is transmitted from the sensor to a data acquisition board and processed in a computer. If the sensor 76 is determined to have proper position, the signals are processed and as output as baseline breathing data 78. If the sensor is not properly placed on the animal, the sensor is adjusted 79 until acceptable baseline signals are obtained. When baseline breathing signals are properly detected, dosing can begin 80. Sensor output is detected 81 by on board system 82 and determines if the signals indicate the start of inhalation. If the signals are not from an inhalation the system continues monitoring until it detects an inhalation upon which the system can trigger actuation of the solenoid to activate the air pump 84. In one embodiment, the insufflation system can be set for a single dose delivery 86. If multiple dosing or repeated doses are to be administered, the system queries if it is the last trigger 86. If it is not the last trigger, the system will continue to detect inhalation signals until all doses are delivered and the output data 88 is displayed on a screen, printed, or saved in the microprocessor or computer system.

Figure 11:
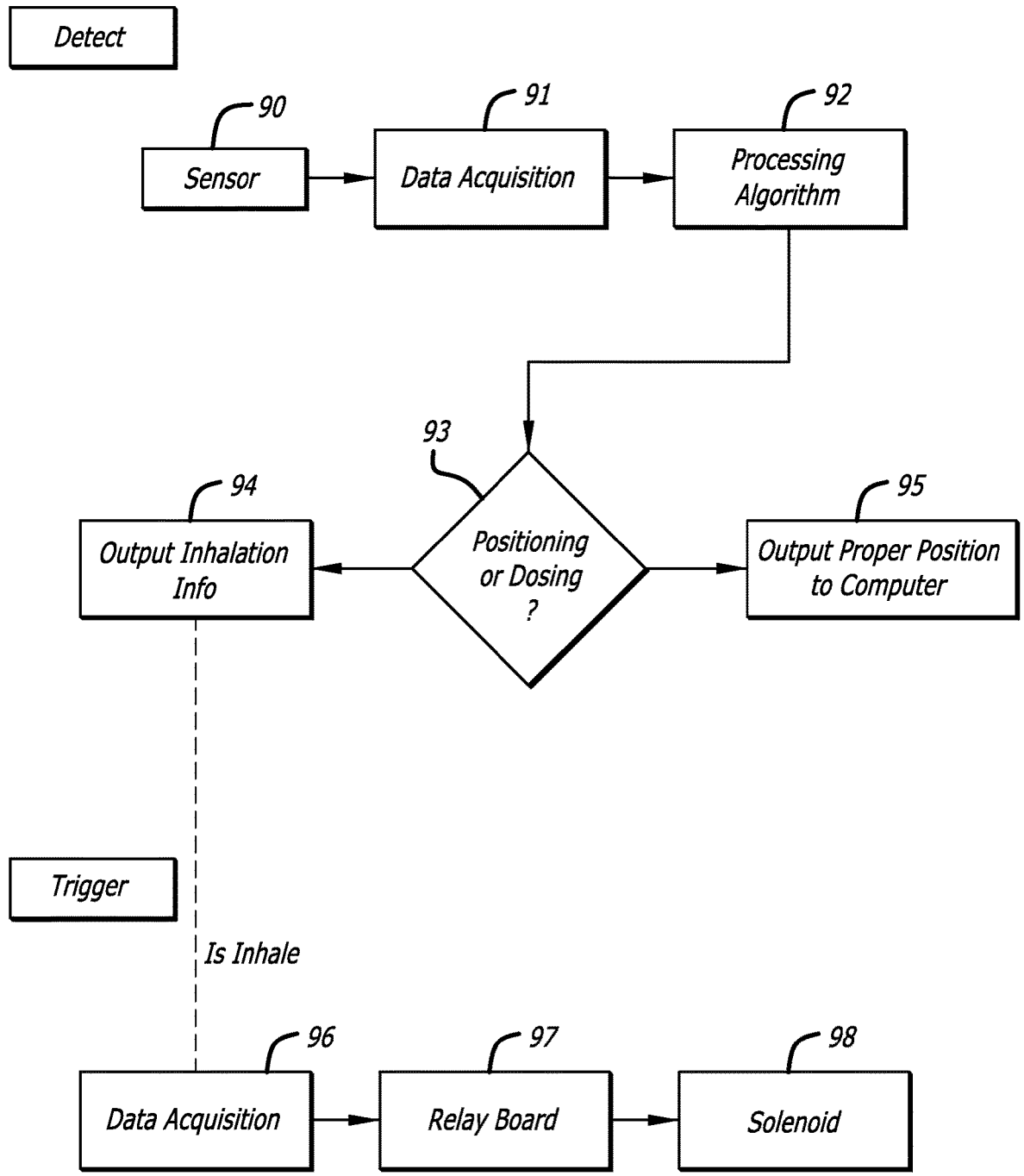
FIG. 11 is a schematic representation of the hardware communication system of an embodiment of the herein described apparatus.

FIG. 11 is a schematic representation of the hardware communication system of an embodiment of the claimed apparatus. Sensor 90 which can be a microphone, accelerometer, thermistor, or transducer sends signals to a data acquisition board 91, which can be part of a microprocessor or a computer module. Signals from the data acquisition board 91 are processed and analyzed using a processing algorithm 92, which detects positioning of the sensor and/or dosing, and also communicates output regarding the breathing patterns of the animal and about proper positioning of sensor and to computer 95. Processing algorithm 92 also analyzes the inhalation information 94 from the animal and if an inhalation is detected, it directs the information to the data acquisition board 96 for further action. The data acquisition board determines if a trigger of an insufflation is required and if so it directs the relay board 97 to actuate the solenoid 98 and activate the air pump to initiate an insufflation as the animal begins an inhalation.

Figure 12:
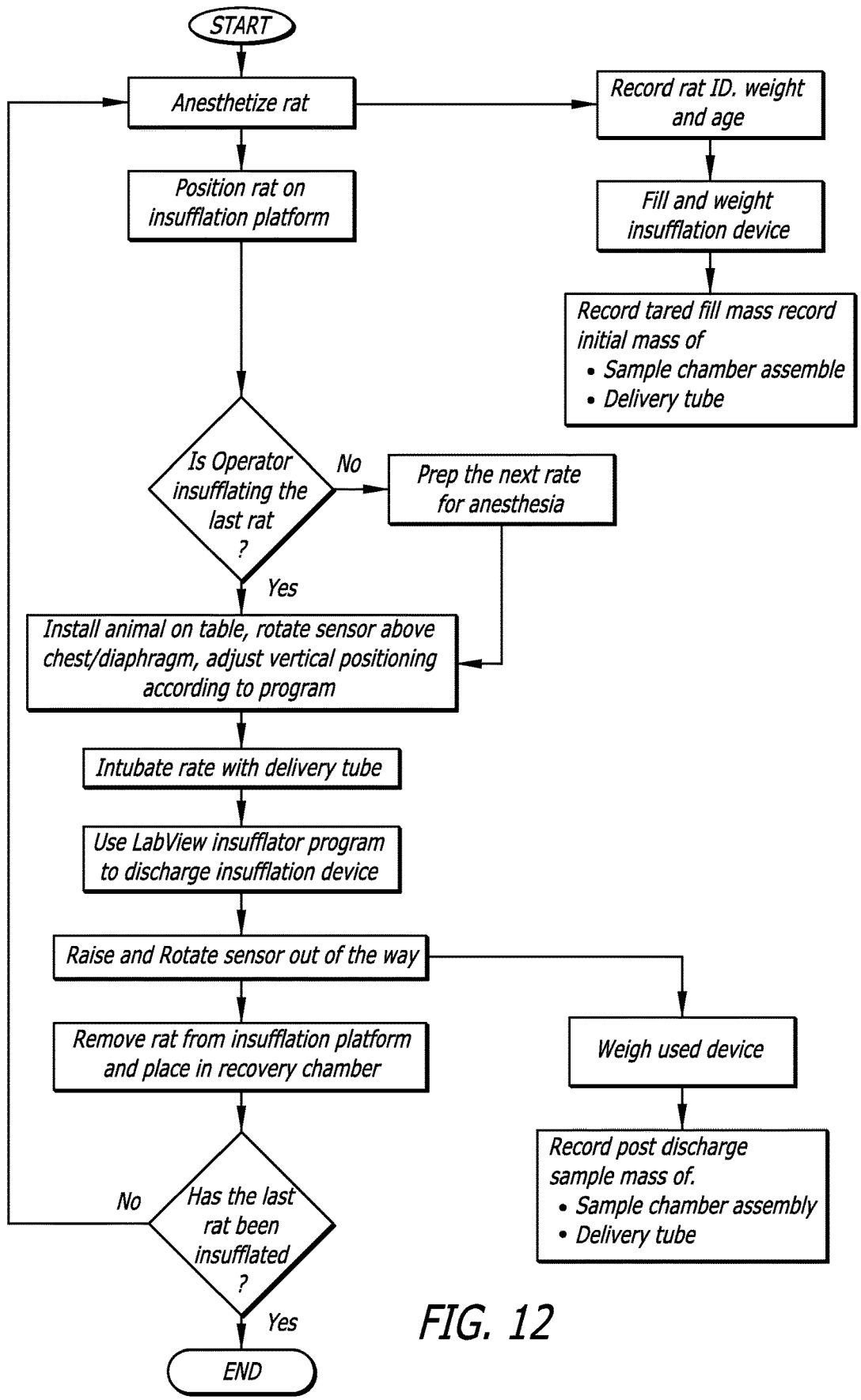
FIG. 12 is schematic representation of the insufflation sequence using an example embodiment apparatus for use with an experimental animal.
Figure 13:
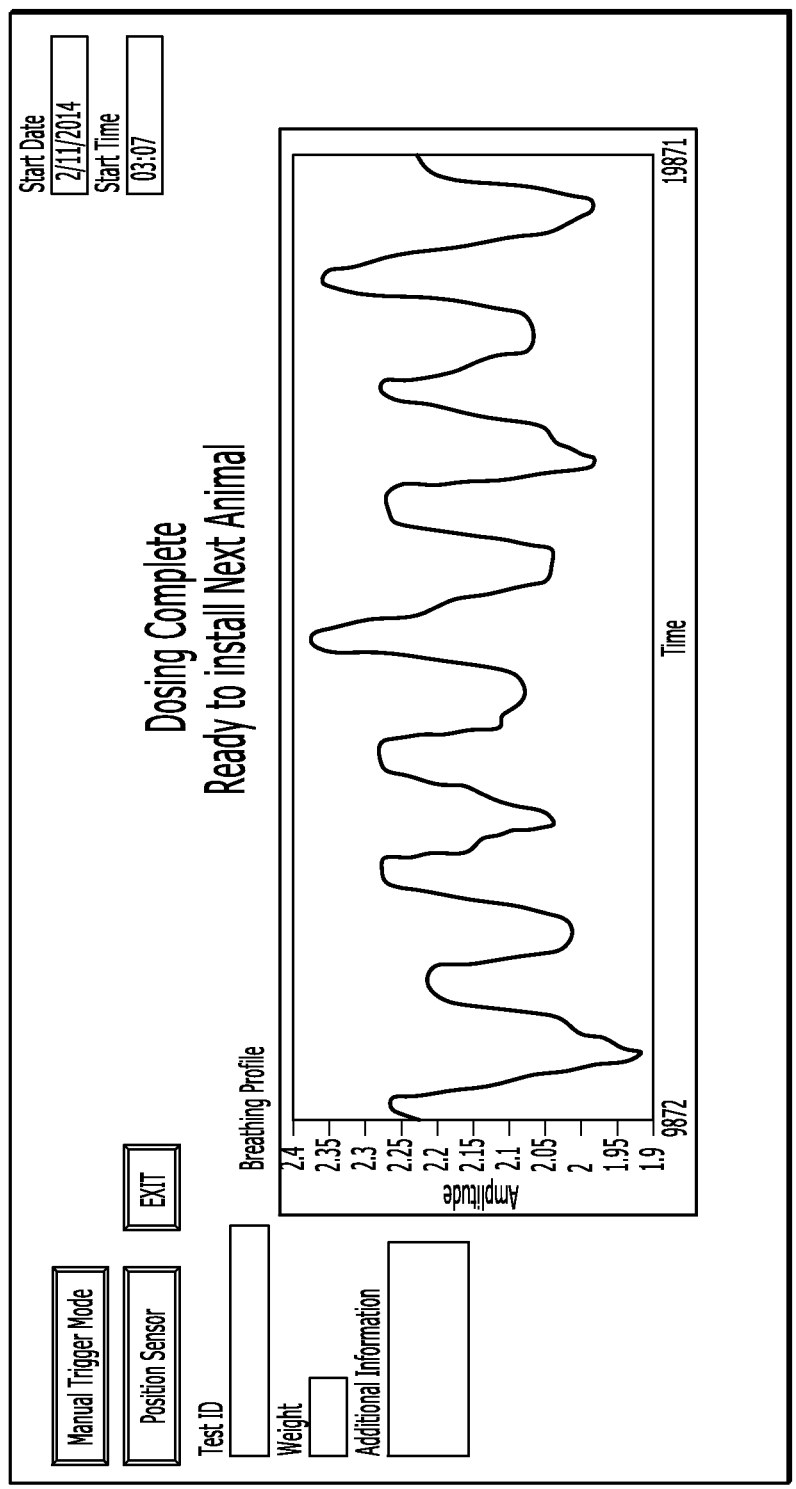
FIG. 13 is a computer screenshot showing an output signal generated from data obtained from an insufflation study with an embodiment apparatus in use during an insufflation of a Sprague Dawley rat as exemplified in FIGS. 8 and 9.

FIG. 12 is schematic representation which summarizes the sequence of steps that are needed to performing an insufflation study using an example embodiment apparatus for use with an experimental small animal, for example, a rat or a mouse.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

EXAMPLE 1

Monitoring and Delivering a Measured Dose of a Powder Composition

The photographs in FIGS. 6A and 6B depict an actual apparatus set up intended for use with a small animal, in this example, the apparatus was designed for use with rodent such as a rat or a mouse. FIG. 6A depicts the insufflation system prototype consisting of a plexiglass and metal stand and a platform. As shown in FIGS. 6A and 6B a portion of the stand is visible, consisting of a Lucite platform attached to a mounting means having supports for holding the platform. For testing purposes, the insufflation apparatus herewith is illustrated using a balloon which was mounted underneath the accelerometer strap to simulate the displacement motion of the abdomen/thorax of a rat or mice during breathing. The balloon is secured to the platform and for undergoing a simulation insufflation procedure. The balloon has been positioned in the same location as the abdomen of the animal that would be in the process of being insufflated. This configuration is to serve as a test which allows to assess the signal captured by the accelerometer mounted at the center of the strap. The balloon is connected to a pressurized air source and a three way valve and can thus be inflated and deflated periodically to mimic the breathing pattern of a small animal.

Figure 7:
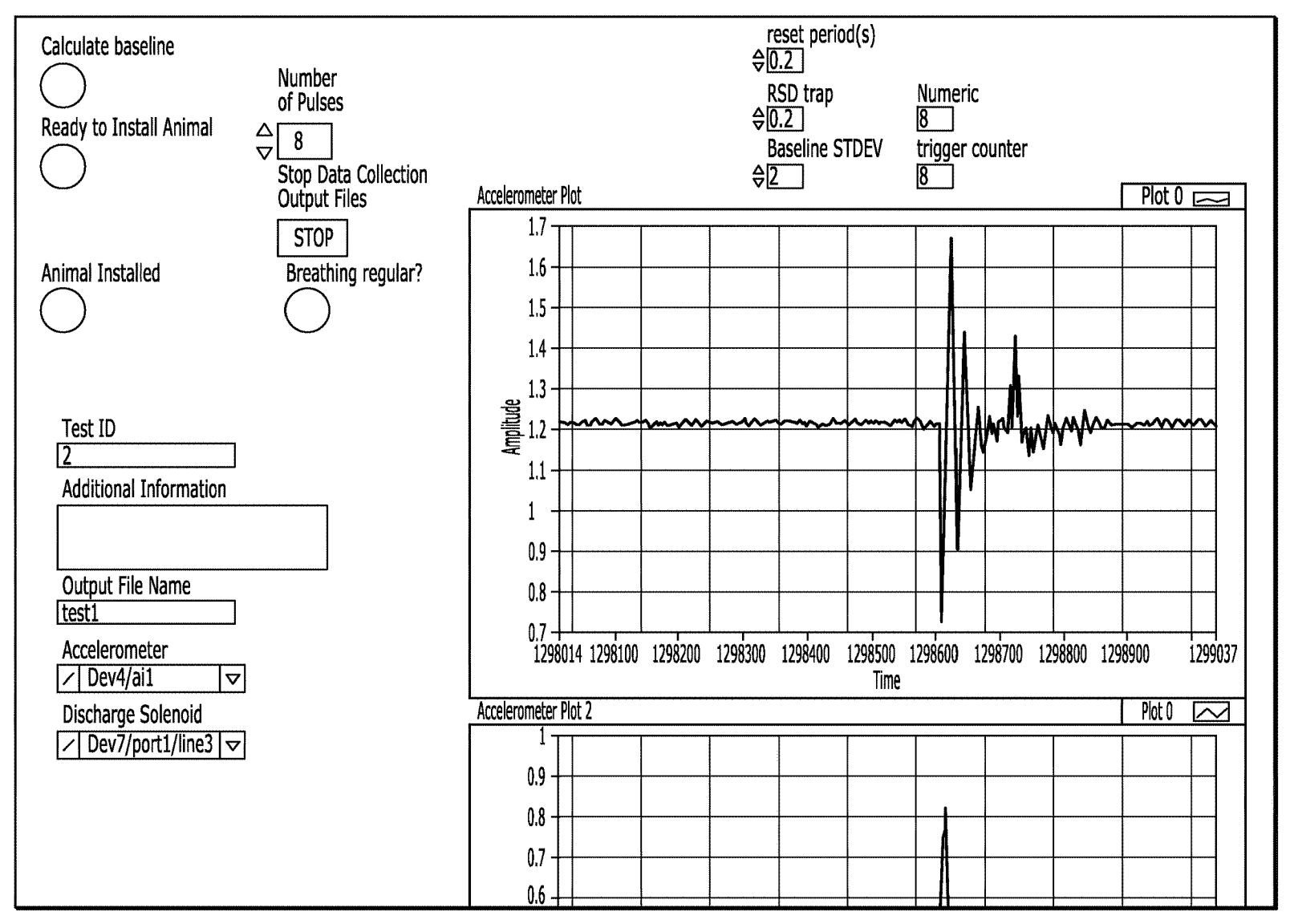

The screenshot in FIG. 7 acquired from an experiment with a balloon shows the control interface with a plot of the data collected from the accelerometer and displayed on a screen. The signal is characterized by a baseline when the balloon is at rest. Upon rapid inflation and deflation of the balloon, the accelerometer measures a rapid changing oscillating signal. The system is then set to actuate the solenoid in the second device, an air pump (not shown) pressurizes the syringe pump to discharge a powder from the powder reservoir at a predetermine interval during a simulated inhalation.

EXAMPLE 2

Insufflation Experiments with Rats

Sprague-Dawley rats were used in these experiments. Rats were anesthetized, intubated and monitored using the insufflation assembly shown in FIGS. 5 and 8, using the method as described in FIGS. 12 and 5 mg of dry powder compositions per kilogram of weight of rat. Administration of the dose to each rat was triggered by the system during natural inhalation as detected by the system. Data collected from these experiments show that the process for intubation and insufflation was achievable for the delivery of doses of neutron activated cerium dioxide (NM-212, Specific Activity=5.7 μCi of $^{141}Ce$/mg $CeO_2$) to the rats during inhalations in a consistent manner data not shown). Table 1 illustrate data obtained from this study.

TABLE 1

Inhalation characteristics during insufflation.

| | | average | | |
|---|---|---|---|---|
| animal ID | # of inhalations | inhalation duration (s) | inhalation cycle (s) | Inhalations per minute |
| rat 25 | 10 | 0.260 | 1.275 | 47.1 |
| rat 26 | 10 | 0.169 | 1.524 | 39.4 |
| rat 27 | 10 | 0.226 | 1.224 | 49.0 |
| rat 28 | 10 | 0.108 | 0.685 | 87.5 |
| rat 29 | 10 | 0.096 | 0.863 | 69.5 |
| rat 30 | 8 | 0.274 | 1.357 | 44.2 |
| rat 31 | 9 | 0.182 | 1.041 | 57.6 |
| rat 32 | 10 | 0.115 | 0.682 | 88.0 |
| rat 33 | 10 | 0.140 | 0.867 | 69.2 |
| rat 34 | 8 | 0.216 | 0.897 | 66.9 |
| rat 35 | 10 | 0.156 | 1.255 | 47.8 |
| rat 36 | 9 | 0.062 | 1.111 | 54.0 |
| | average | 0.167 | 1.065 | 56.3 |

The data in Table 1 shows that the breathing cycles detected by the apparatus herein are greater than 0.5 seconds. Specifically, the data shows the rats breathing cycles detected indicated that the rats were breathing at intervals between 0.68 and 1.52 seconds with inhalations lasting from about 62 to about 300 milliseconds.

FIG. 13 is a computer screenshot showing an output signal generated from data obtained from an insufflation study with an embodiment apparatus in use during an insufflation of a Sprague Dawley rat describe herewith. As seen in FIG. 13, each breathing cycle for the rat is shown from valley to valley in a real-time plot of the data collected with a linear position sensor as described in FIGS. 8 and 9.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A dry powder drug delivery system, comprising:
a single platform structurally configured for receiving an anesthetized animal and mounted on a stand comprising a base and support beams adapted with a hinge configured to hold said single platform, and a shaft configured to hold and support an air pump comprising: said air pump
adapted with a linear solenoid, and a powder reservoir; wherein said linear solenoid is actuated by an onboard relay output system to pressurize a syringe pump at a predetermined interval during an inhalation to release a powder plume from the powder reservoir;
a drug delivery device adapted to said air pump and comprising a cannula for positioning in a mouth and a chamber for containing a dry powder drug composition;
an adjustable strap comprising one or more sensors for detecting breathing cycles of the anesthetized animal, wherein at least one of the one or more sensors is an accelerometer, a microphone, a thermistor, and/or a transducer;
a data acquisition board comprising an executable algorithm for analyzing and transmitting signals from said one or more sensors and determining and displaying the anesthetized animal's breathing pattern, wherein said executable algorithm contains instructions to actuate said linear solenoid at a predetermined interval of a breathing cycle of said anesthetized animal and delivers an aerosolized dry powder composition to the anesthetized animal during an inhalation; and
wherein said single platform comprises a hanging wire, neck support posts, and said adjustable strap to position said anesthetized animal on said single platform.

2. The system of claim 1, including a second sensor configured to detect the anesthetized animal's breathing.

3. An apparatus, comprising:
a first device comprising a single platform comprising an animal positioning area comprising a hanging wire and neck support posts to support and align a neck of an anesthetized animal and an adjustable strap including one or more sensors which detect distention of said anesthetized animal's abdomen and/or thorax due to breathing, generates an input signal and communicates the input signal to a microprocessor for analysis wherein at least one of the one or more sensors is an accelerometer, a microphone, a thermistor, and/or a transducer wherein said adjustable strap is positioned over a diaphragm of said anesthetized animal; and
a second device comprising a linear solenoid, a syringe pump and a drug delivery device adapted to an air pump and comprising a cannula for positioning in a mouth and a chamber for containing a dry powder drug composition;
wherein said linear solenoid is actuated by an onboard relay output system to pressurize the syringe pump;
wherein said second device further comprises a computer interface comprising a programmable algorithm which detects, analyzes and sends instructions of the anesthetized animal's breathing pattern and actuates said linear solenoid to pressurize the syringe pump at a predetermined interval during an inhalation to release a powder plume from the chamber
wherein said single platform is mounted on a stand comprising a base and support beams adapted with a hinge configured to hold said single platform, and a shaft configured to hold and support said air pump.

4. The apparatus of claim 3, further comprising a mount to secure said single platform.

5. The apparatus of claim 3, wherein said first device further comprises a second sensor, which is configured to detect the anesthetized animal's breathing.

6. An insufflation method comprising:
positioning an anesthetized animal on a single platform of an insufflation apparatus comprising an automated air pump syringe adapted with a linear solenoid and a drug delivery device comprising a cannula for positioning in a mouth and a chamber for containing a dry powder drug composition wherein said single platform includes a hanging wire and neck support posts to support and align a neck of said anesthetized animal, and an adjustable strap, and is mounted on a stand comprising a base and support beams adapted with a hinge configured to hold said single platform, and a shaft configured to hold and support said air pump syringe;
placing said adjustable strap comprising one or more sensors on or near the anesthetized animal to detect breathing signals of said anesthetized animal, wherein the sensors are configured to detect and transmit the breathing signals and communicate with a data acquisition board, and wherein at least one of the one or more sensors is an accelerometer, a microphone, a thermistor, or a transducer wherein said adjustable strap is positioned over a diaphragm of said anesthetized animal; and
analyzing the breathing signals from the anesthetized animal's breathing cycles to determine and analyze the anesthetized animal's breathing rate and cycles in real-time using a microprocessor with an executable algorithm, and administering a dose of the dry powder drug composition at an inhalation interval by actuating the linear solenoid to generate a predetermined force at a predetermined interval of an inhalation of the anesthetized animal's breathing cycle.

7. The method of claim 6, wherein actuating the linear solenoid is carried out from signals from a computer interface comprising a programmable algorithm.

8. The method of claim 6, wherein actuating the linear solenoid generates air pressure in the air pump syringe which discharges the dose of a test composition.

9. The method of claim 6, further comprising intubating the anesthetized animal with the cannula from the insufflation device.

10. The method of claim 6, wherein placing of the one or more sensors on or near the anesthetized animal is automated.

* * * * *